(12) United States Patent
Muthusamy et al.

(10) Patent No.: US 11,066,390 B2
(45) Date of Patent: Jul. 20, 2021

(54) SOLID STATE FORMS OF IVOSIDENIB

(71) Applicant: ASSIA CHEMICAL INDUSTRIES LTD., Petach Tikva (IL)

(72) Inventors: Anantha Rajmohan Muthusamy, Sivakasi (IN); Amit Singh, Greater Noida (IN); Venkata Subbarao Yazali, Guntur (IN); Parven Kumar Luthra, New Delhi (IN); Sanjay Lakhabhai Vasoya, Rajkot (IN); Bhatu Tumba Patil, Greater Noida (IN); Amit Kumar Taneja, Yamunanagar District (IN); Naveen Chandra Srivastav, Greater Noida (IN); Rinku Singh, Noida (IN); Vadivelan Rengasamy, Ariyalur District (IN); Abhilash Tyagi, Greater Noida (IN)

(73) Assignee: ASSIA CHEMICAL INDUSTRIES LTD., Petach Tikva (IL)

( * ) Notice: Subject to any disclaimer, the term of this patent is extended or adjusted under 35 U.S.C. 154(b) by 0 days.

(21) Appl. No.: 16/767,176

(22) PCT Filed: Nov. 27, 2018

(86) PCT No.: PCT/US2018/062598
§ 371 (c)(1),
(2) Date: May 27, 2020

(87) PCT Pub. No.: WO2019/104318
PCT Pub. Date: May 31, 2019

(65) Prior Publication Data
US 2020/0308146 A1    Oct. 1, 2020

(30) Foreign Application Priority Data

| Nov. 27, 2017 | (IN) | 201711042475 |
| Dec. 7, 2017 | (IN) | 201711044047 |
| Jan. 5, 2018 | (IN) | 201811000614 |
| Feb. 8, 2018 | (IN) | 201811004740 |
| Mar. 27, 2018 | (IN) | 201811011325 |
| Oct. 24, 2018 | (IN) | 201811040154 |

(51) Int. Cl.
*C07D 401/14* (2006.01)

(52) U.S. Cl.
CPC ........ *C07D 401/14* (2013.01); *C07B 2200/13* (2013.01)

(58) Field of Classification Search
CPC .................................................... C07D 401/14
See application file for complete search history.

(56) References Cited

FOREIGN PATENT DOCUMENTS

| WO | 2013107291 A1 | 7/2013 |
| WO | 2015138839 A1 | 9/2015 |

OTHER PUBLICATIONS

Popovici-Muller "Discovery of AG-120 (Ivosidenib): A First-in-Class Mutant IDH1 Inhibitor for the Treatment of IDH1 Mutant Cancers." ACS Medicinal Chemistry Letters, 2018, 9(4), 300-305.*
Matthew L. Peterson et. al. "Expanding the Scope of Crystal Form Evaluation in Pharmaceutical Science" Journal of Pharmacy & Pharmaceutical Science 2006 (9(3):317-326.*
Zell et. al. "Investigation of Polymorphism in Aspartame and Neotame Using Solid-State NMR Spectroscopy." Tetrahedron 2000, 56, 6603-6616.*
Morrisette "Elucidation of crystal form diversity of the HIV protease inhibitor ritonavir by high-throughput crystallization" Proceedings of the National Academy of Sciences 2003 100( 5) 2180-2184.*
Janeta Popovici-Muller et al. "Discovery of AG-120 (Ivosidenib): A First-in-Class Mutant IDHI Inhibitor for the Treatment of IDH Mutant Cancers", ACS Medicinal Chemistry Letters, vol. 9, No. 4, Jan. 19, 2018 , pp. 300-305.
Stacie Lynn Richardson, "The Ugi Multicomponent Reaction: Stereocontrol, Modifications and Applications", Feb. 19, 2007.
Uli Kazmaier et al. "Peptide Syntheses via Ugi Reactionswith Ammonia", Synlett, No. 11, Jan. 1, 2003 , pp. 1591-1594.
Ivar Ugi et al. "Isonitrile, I. Darstellung von Isonitrilen aus monosubstituierten Formamiden durch Wasserabspaltung", Chemische Berichte, vol. 93, No. 1, Jan. 1, 1960, pp. 239-248.
International Search Report and Written Opinion of the International Searching Authority issued in corresponding Appl. No. PCT/US2018/062598 dated Mar. 4, 2019 (24 pages).

* cited by examiner

*Primary Examiner* — David K O'Dell
(74) *Attorney, Agent, or Firm* — Carter, DeLuca & Farrell LLP

(57) ABSTRACT

Solid state forms of Ivosidenib, processes for preparation thereof, pharmaceutical compositions thereof, and uses thereof are disclosed.

5 Claims, 19 Drawing Sheets

Figure 1: An X-ray powder diffractogram (XRPD) of amorphous Ivosidenib
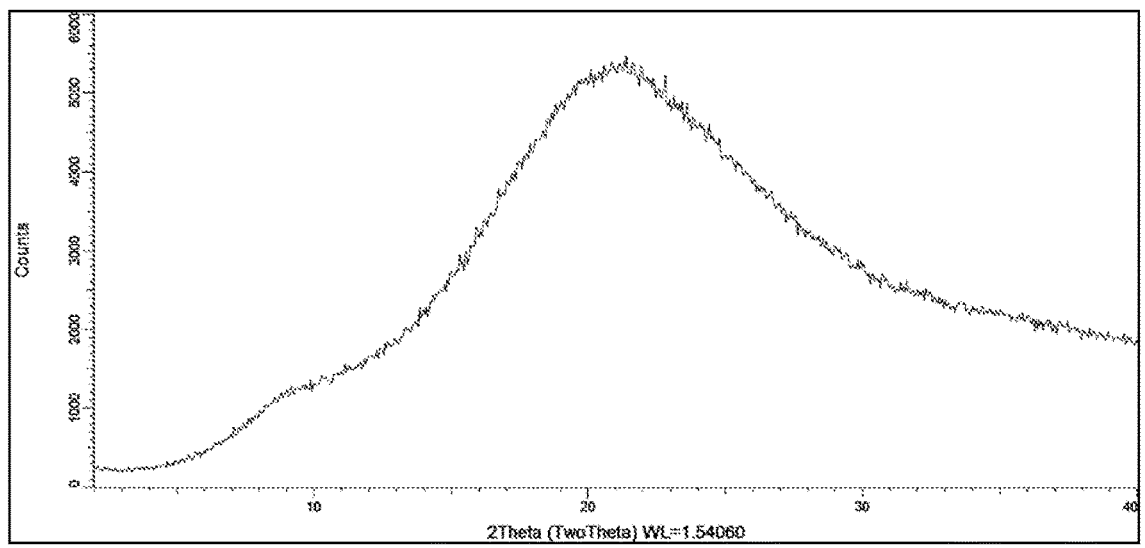
Figure 2: An X-ray powder diffractogram (XRPD) of Form T1 of Ivosidenib
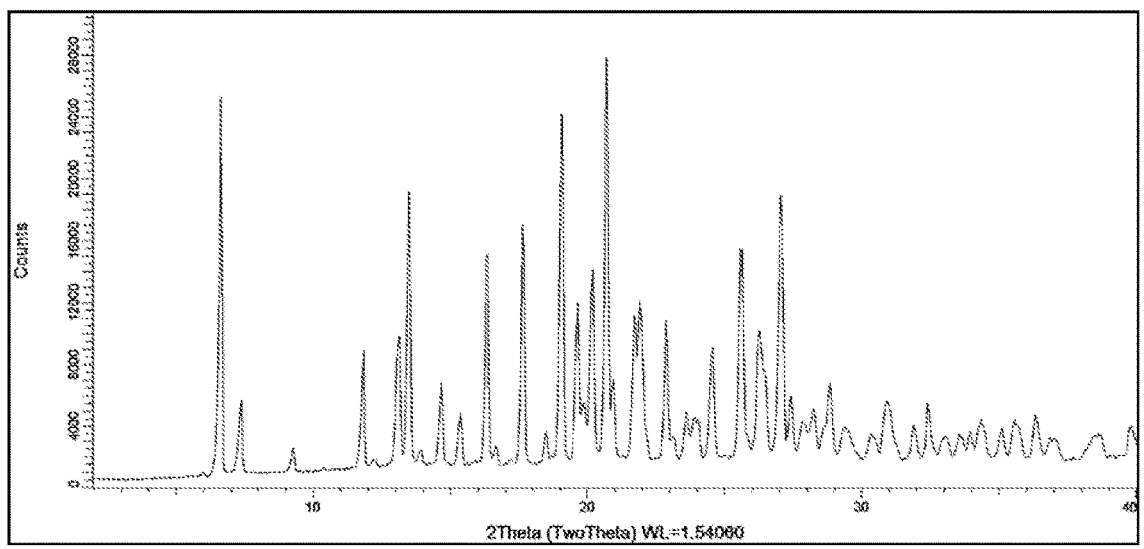

Figure 3: An X-ray powder diffractogram (XRPD) of Form T2 of Ivosidenib
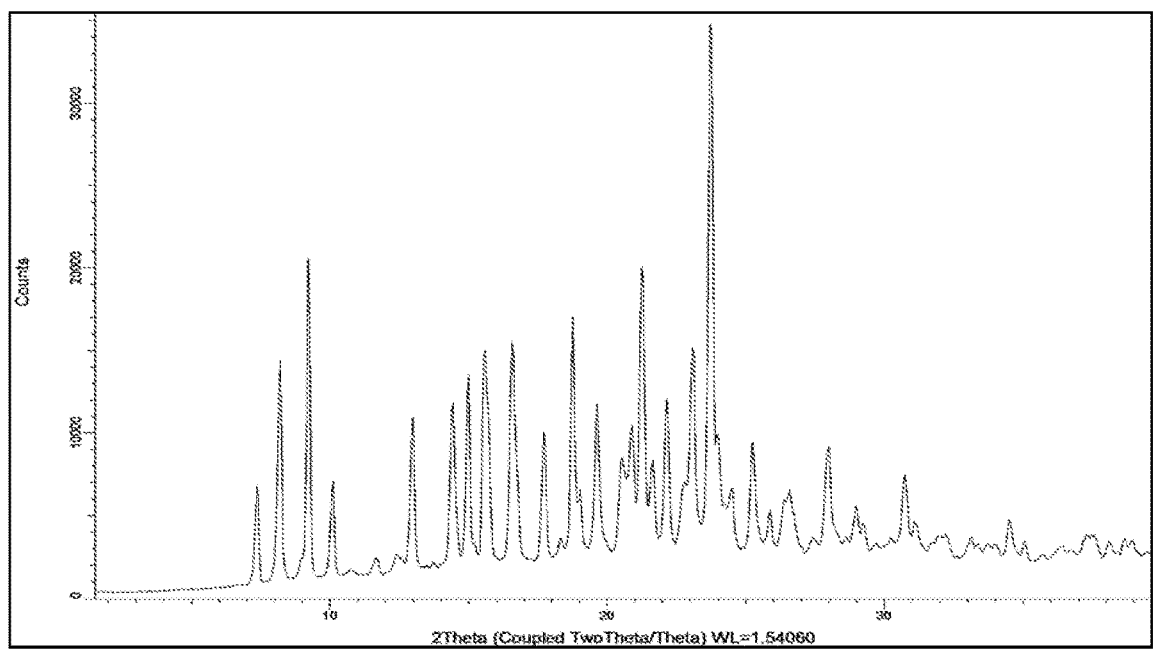
Figure 4: An X-ray powder diffractogram (XRPD) of Form T3 of Ivosidenib
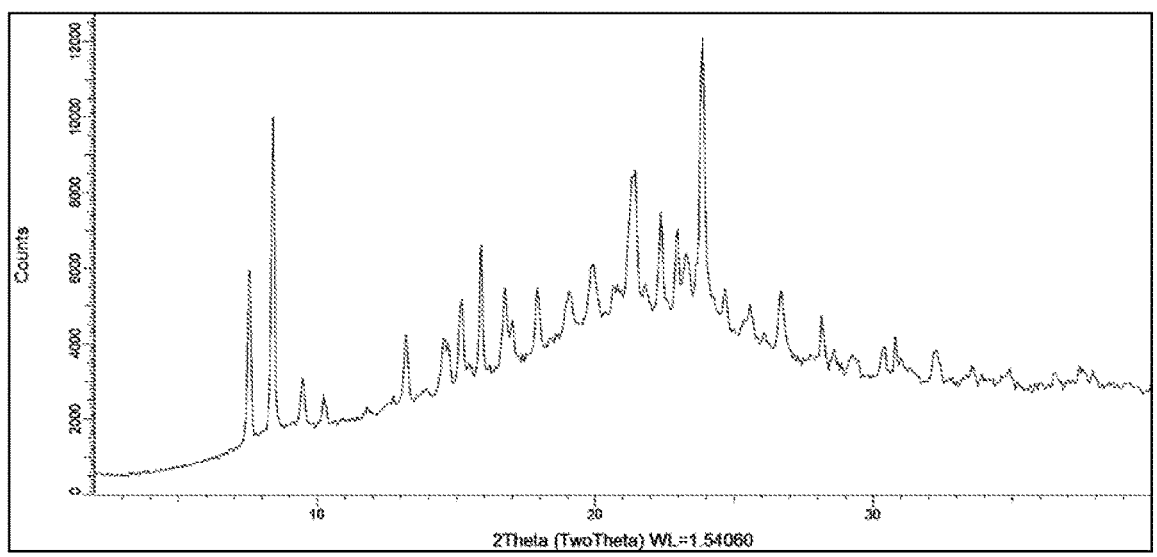

Figure 5: An X-ray powder diffractogram (XRPD) of Form T4 of Ivosidenib
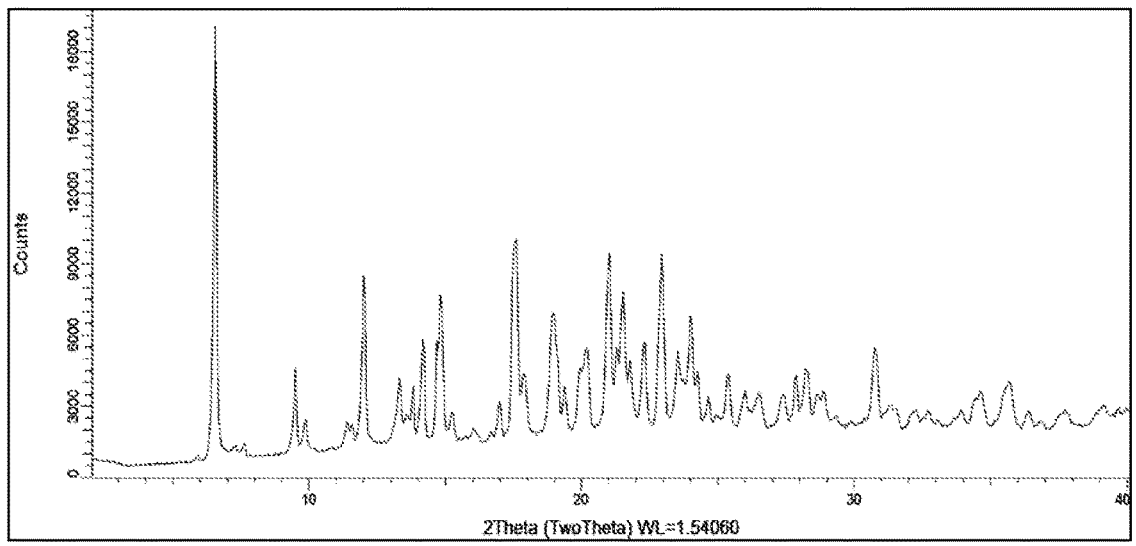
Figure 6: An X-ray powder diffractogram (XRPD) of Form T5 of Ivosidenib
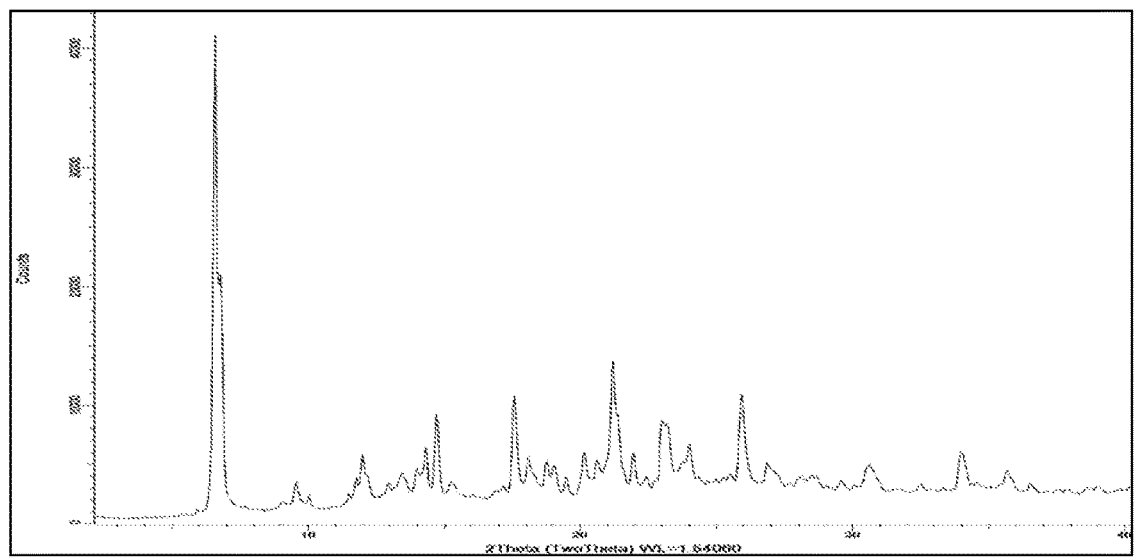

Figure 7: An X-ray powder diffractogram (XRPD) of Form T6 of Ivosidenib
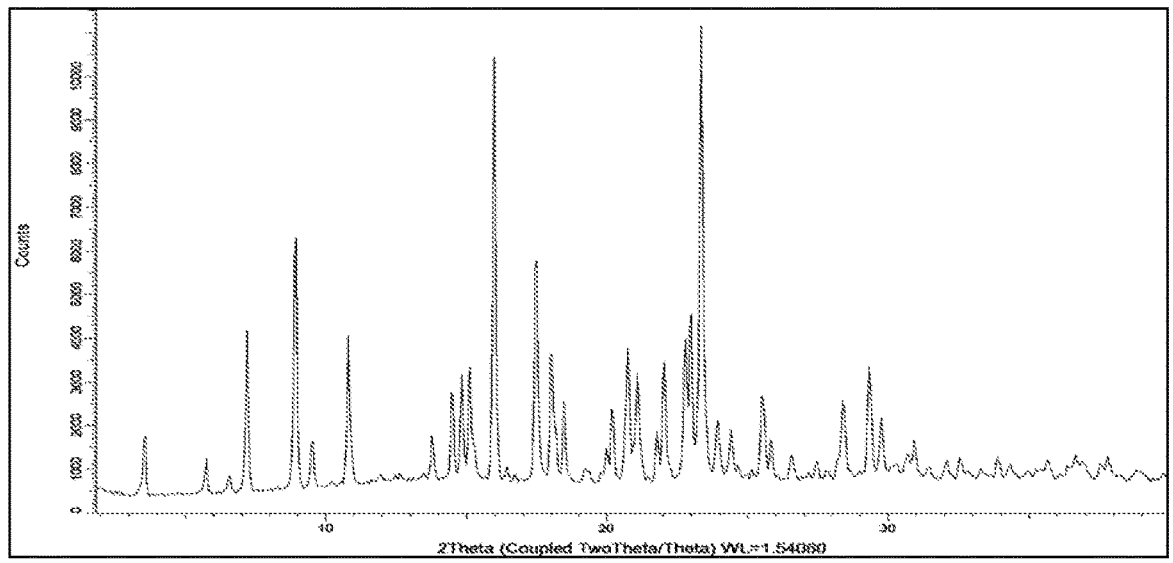
Figure 8: An X-ray powder diffractogram (XRPD) of Form T7 of Ivosidenib
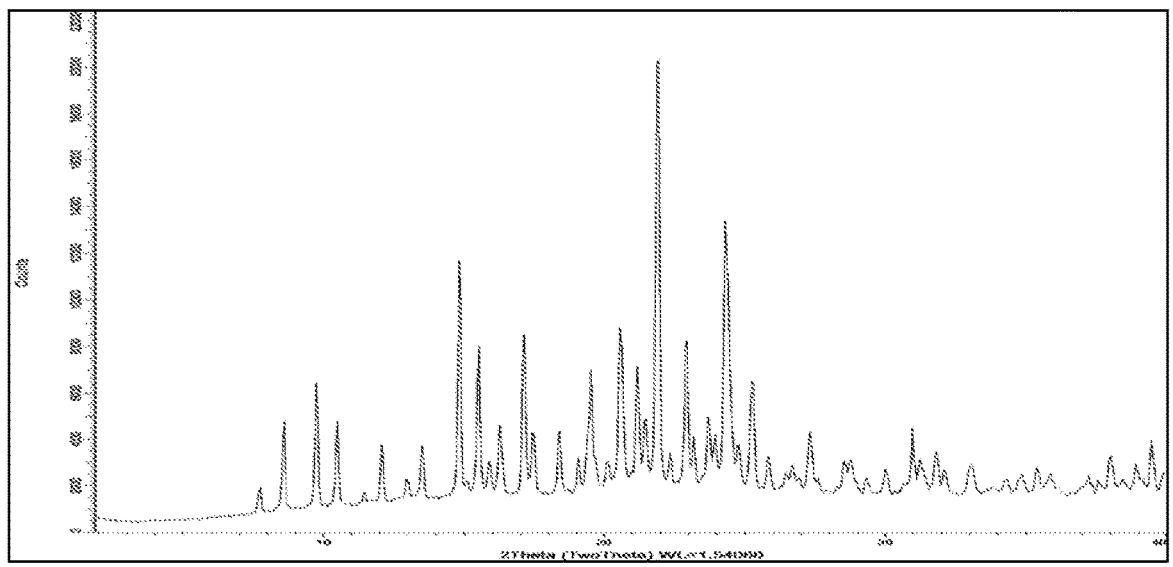

Figure 9: An X-ray powder diffractogram (XRPD) of Form T8 of Ivosidenib
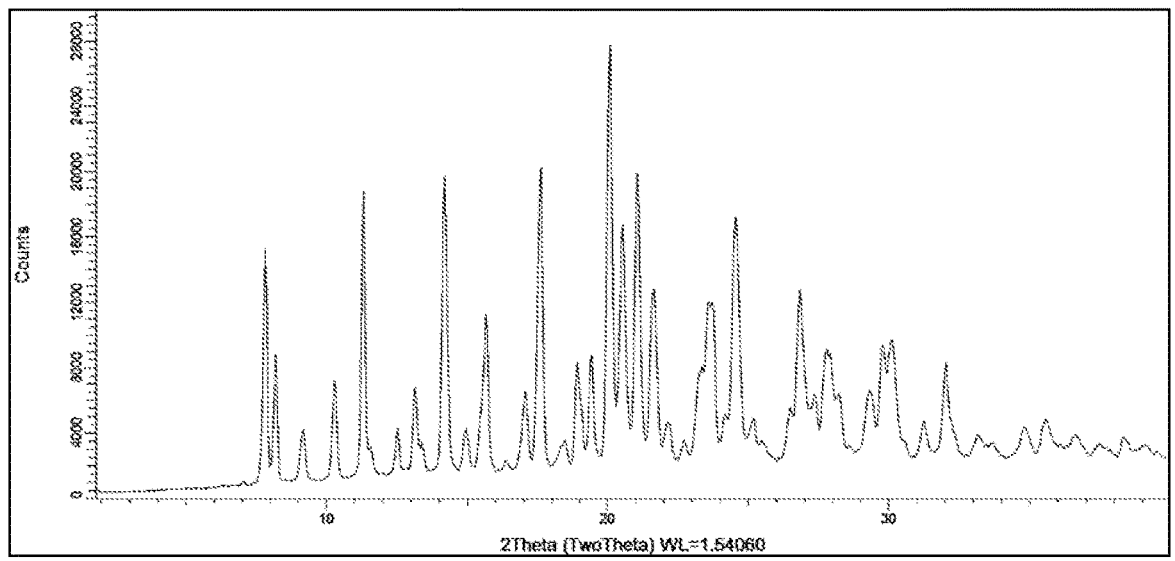
Figure 10: An X-ray powder diffractogram (XRPD) of Form T9 of Ivosidenib
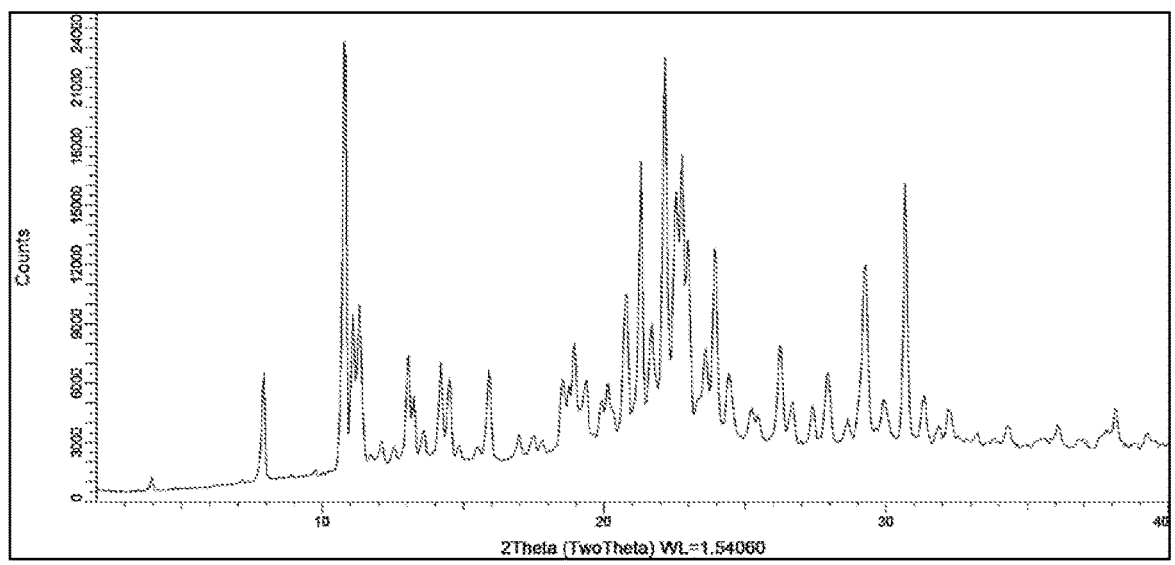

Figure 11: An X-ray powder diffractogram (XRPD) of Form T10 of Ivosidenib
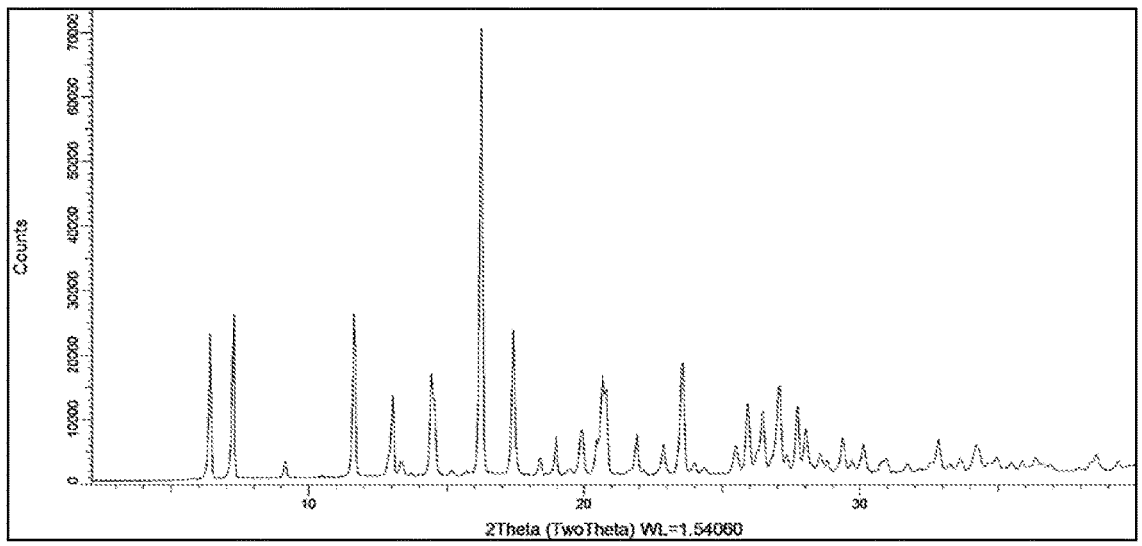
Figure 12: An X-ray powder diffractogram (XRPD) of Form T11 of Ivosidenib
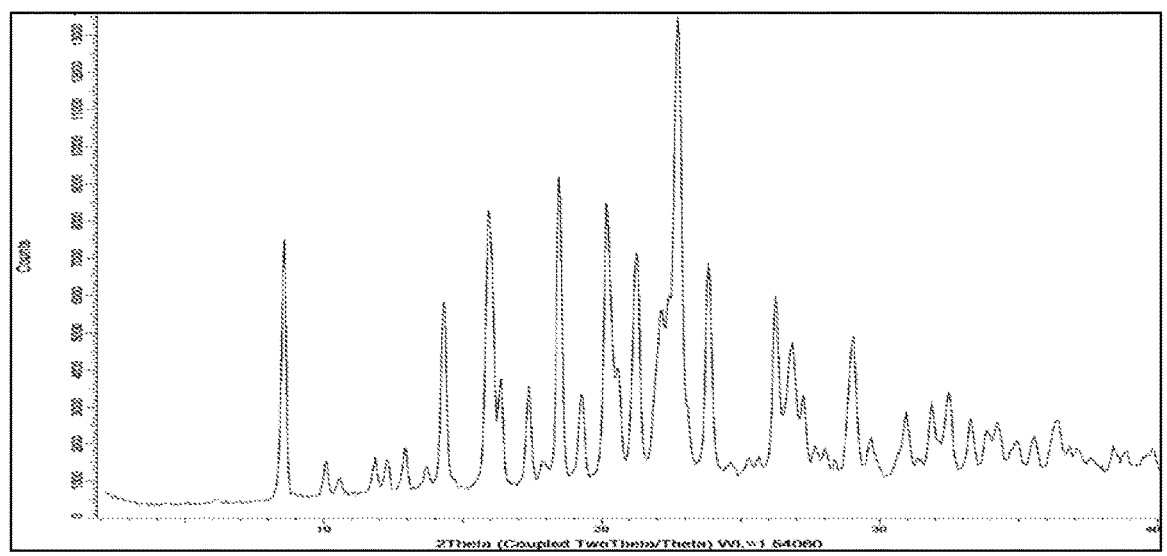

Figure 13: An X-ray powder diffractogram (XRPD) of Form T12 of Ivosidenib
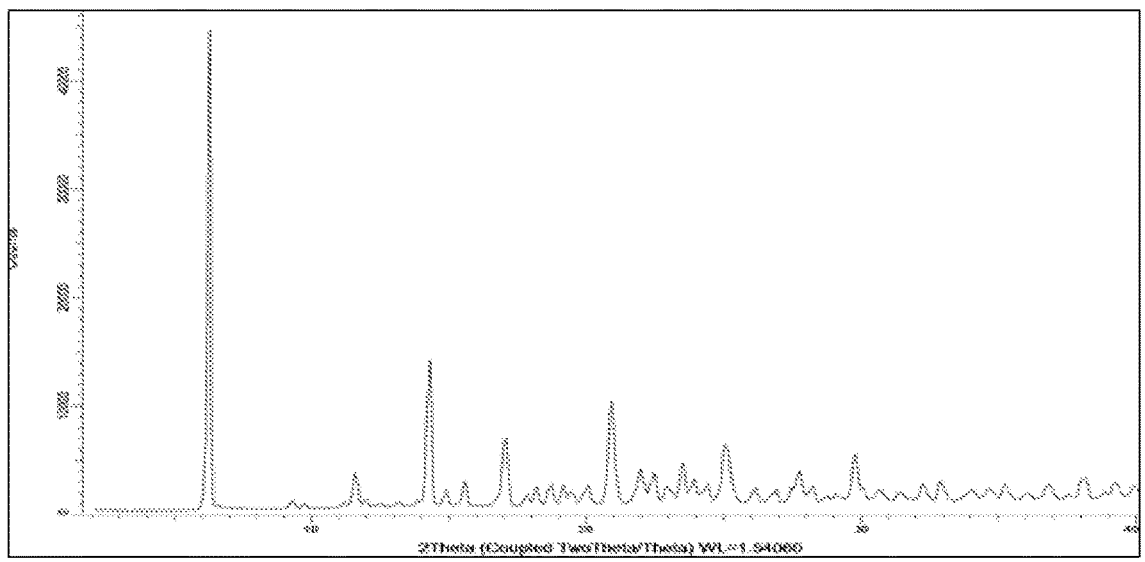
Figure 14: An X-ray powder diffractogram (XRPD) of Form T13 of Ivosidenib
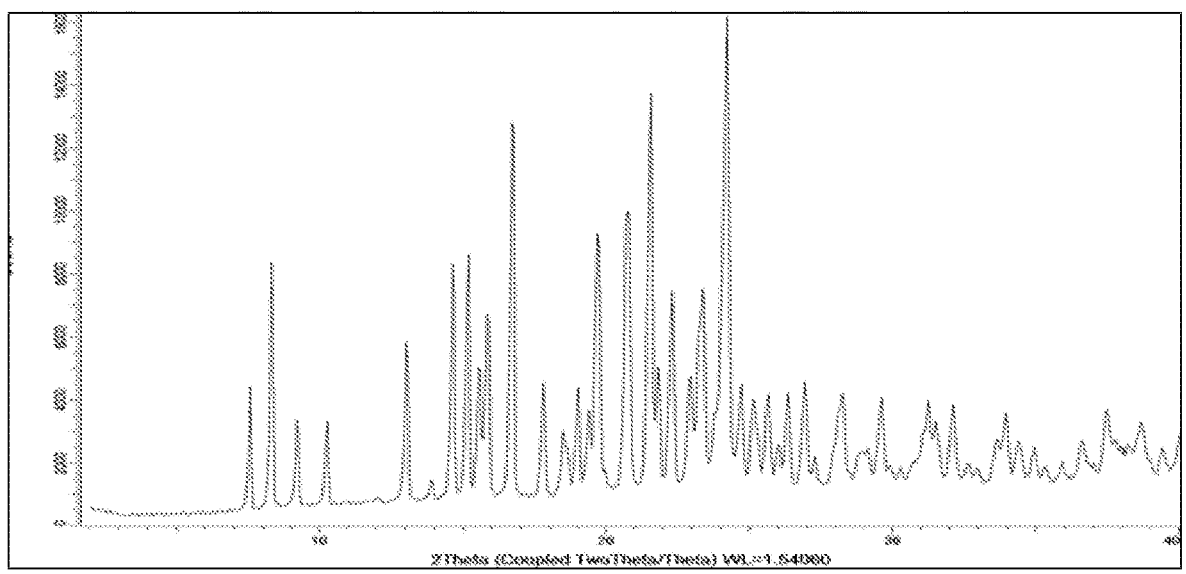

Figure 15: An X-ray powder diffractogram (XRPD) of Form T14 of Ivosidenib
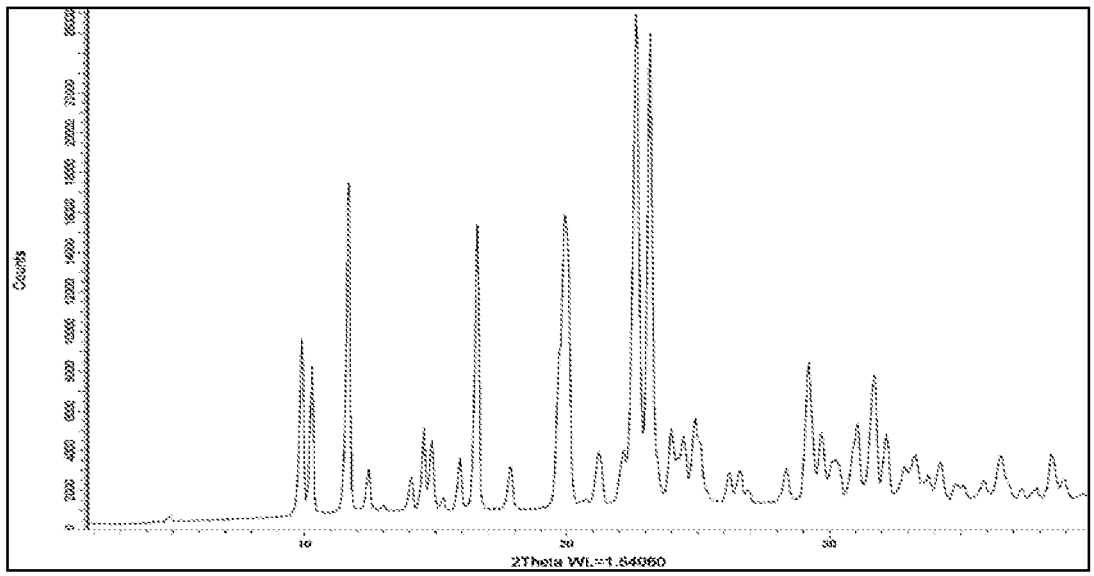
Figure 16: A thermogravimetric analysis (TGA) thermogram spectrum of Form T14 of Ivosidenib
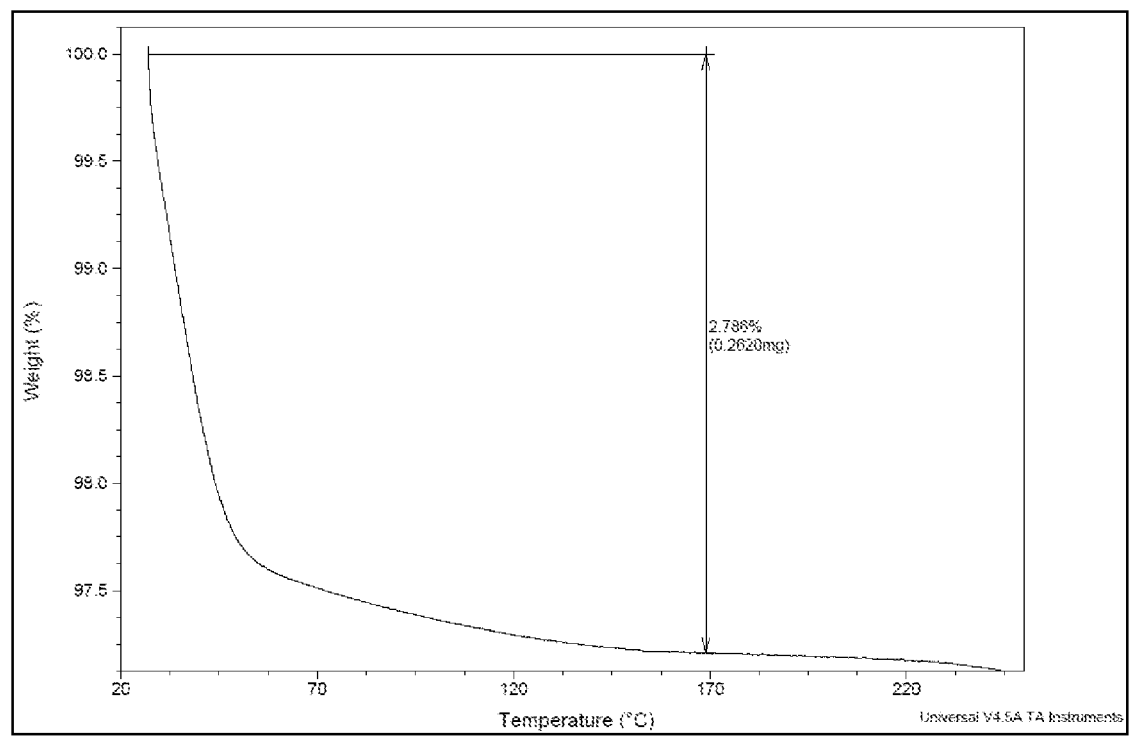

Figure 17: An X-ray powder diffractogram (XRPD) of Form T15 of Ivosidenib
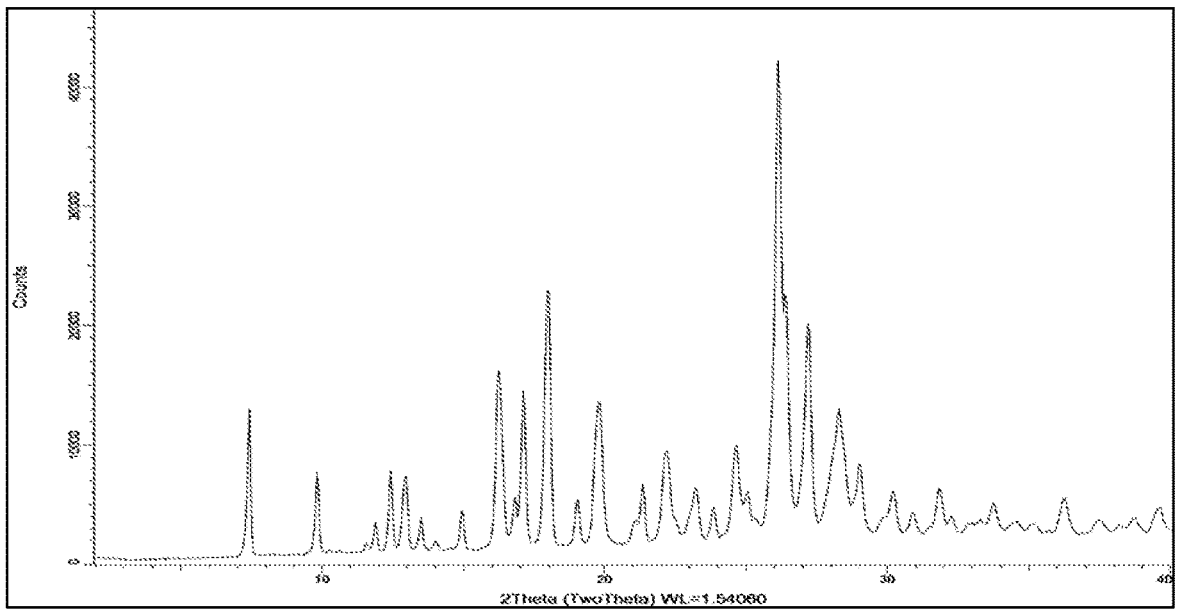
Figure 18: A thermogravimetric analysis (TGA) thermogram spectrum of Form T15 of Ivosidenib
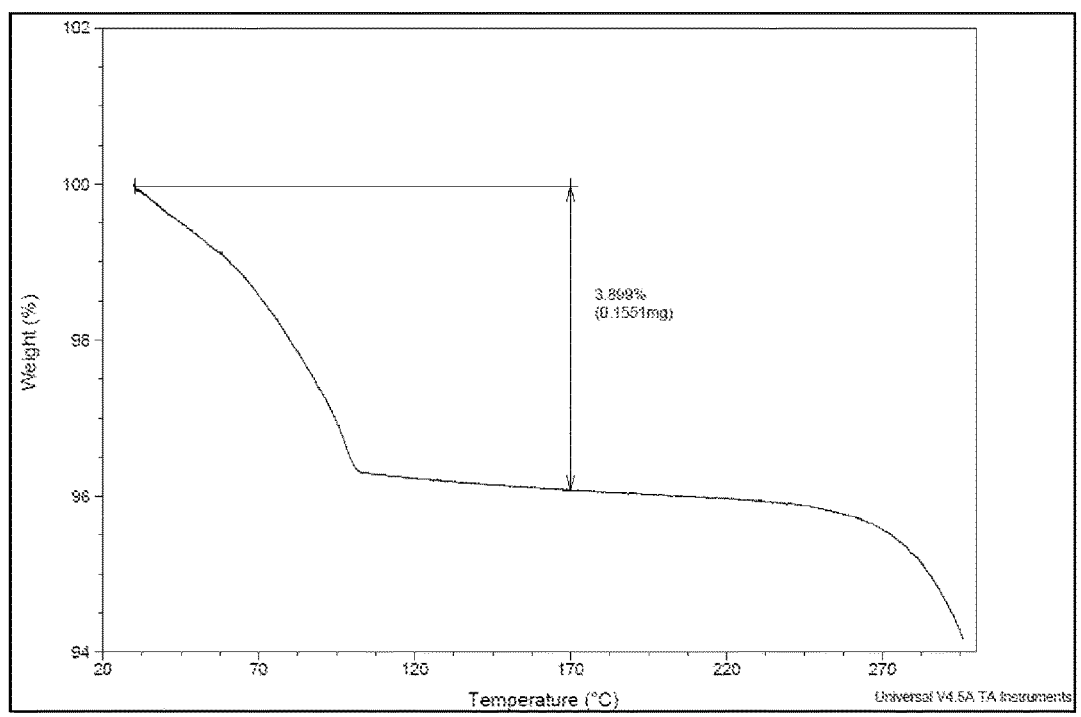

Figure 19: An X-ray powder diffractogram (XRPD) of Form T16 of Ivosidenib
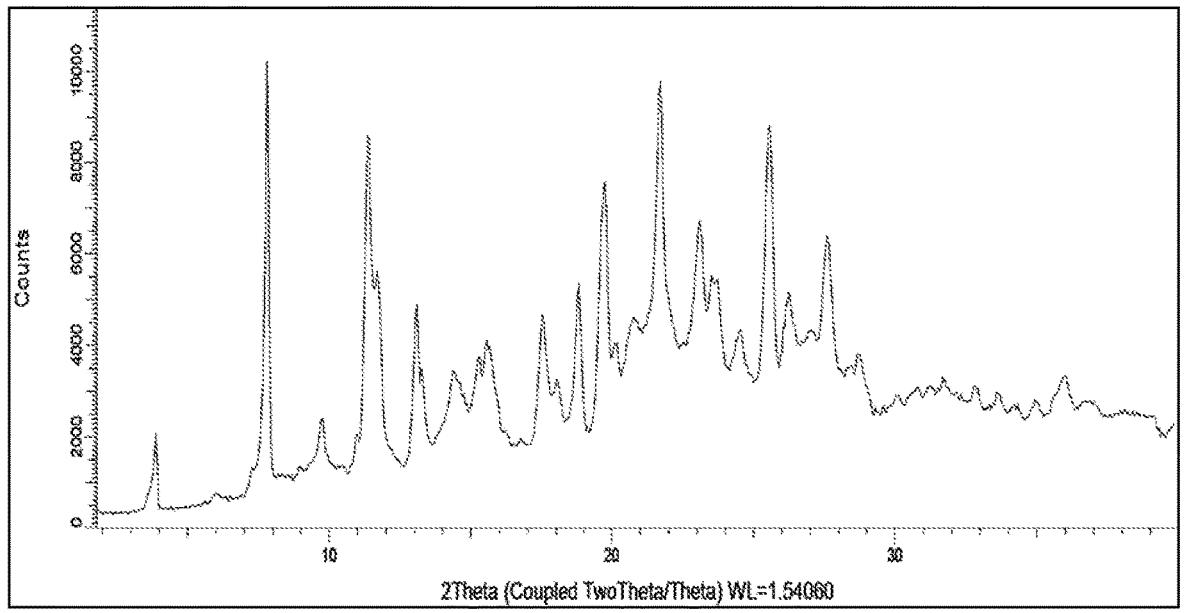
Figure 20: An X-ray powder diffractogram (XRPD) of Form T17 of Ivosidenib
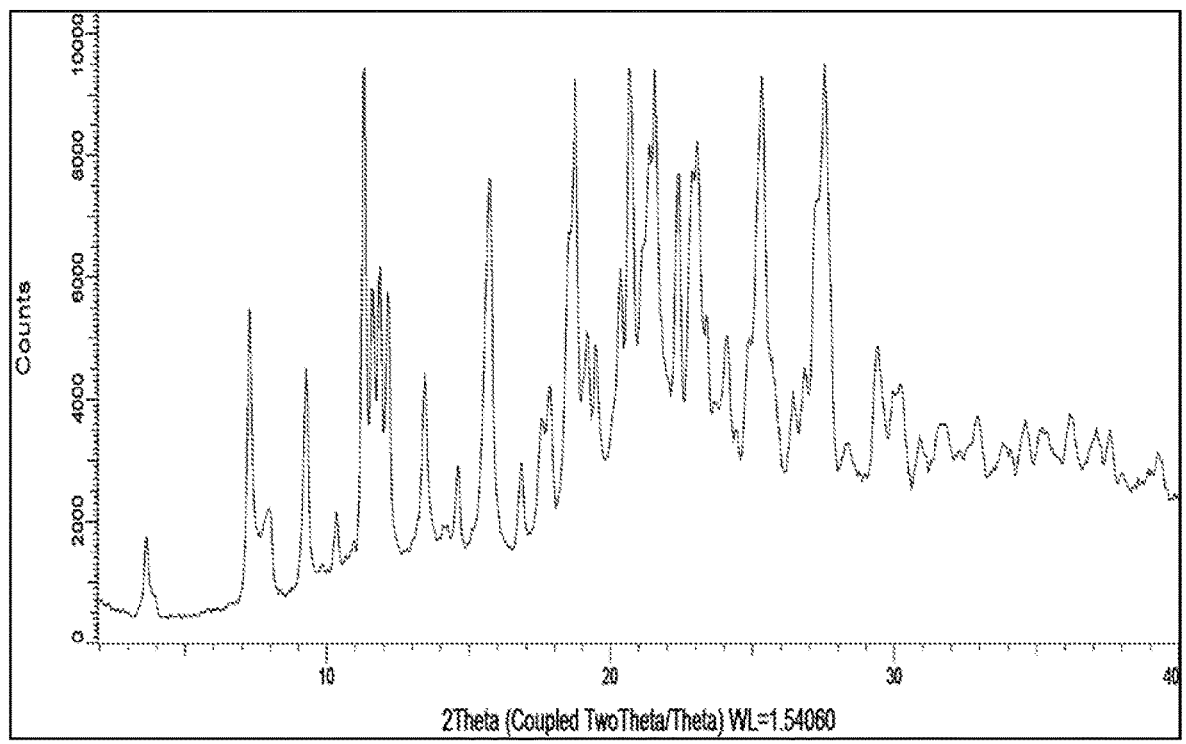

Figure 21: An X-ray powder diffractogram (XRPD) of Form T18 of Ivosidenib
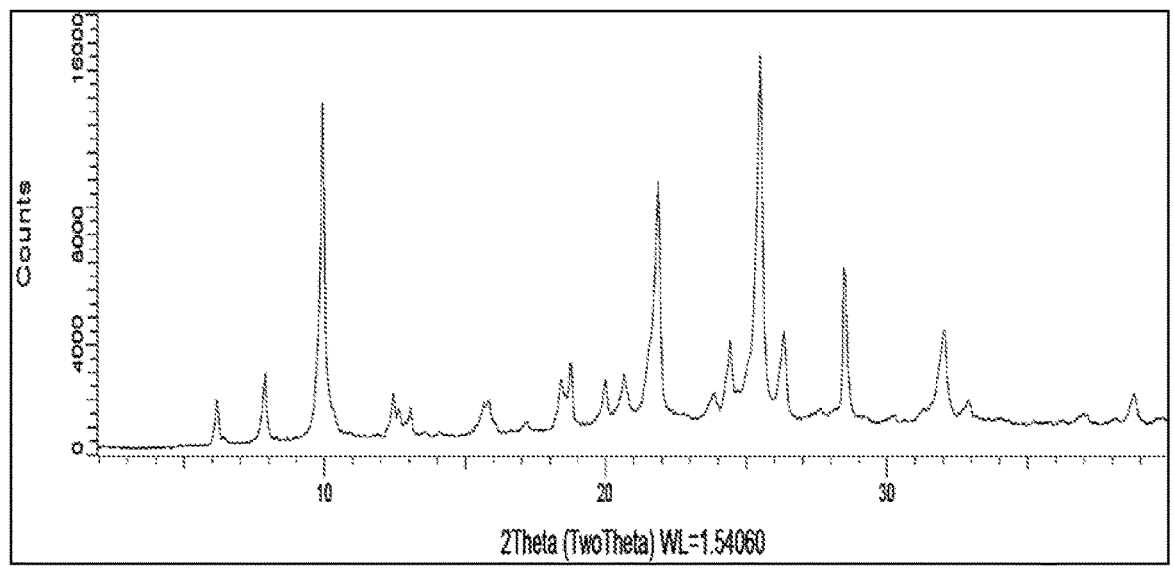
Figure 22: An X-ray powder diffractogram (XRPD) of Form T19 of Ivosidenib
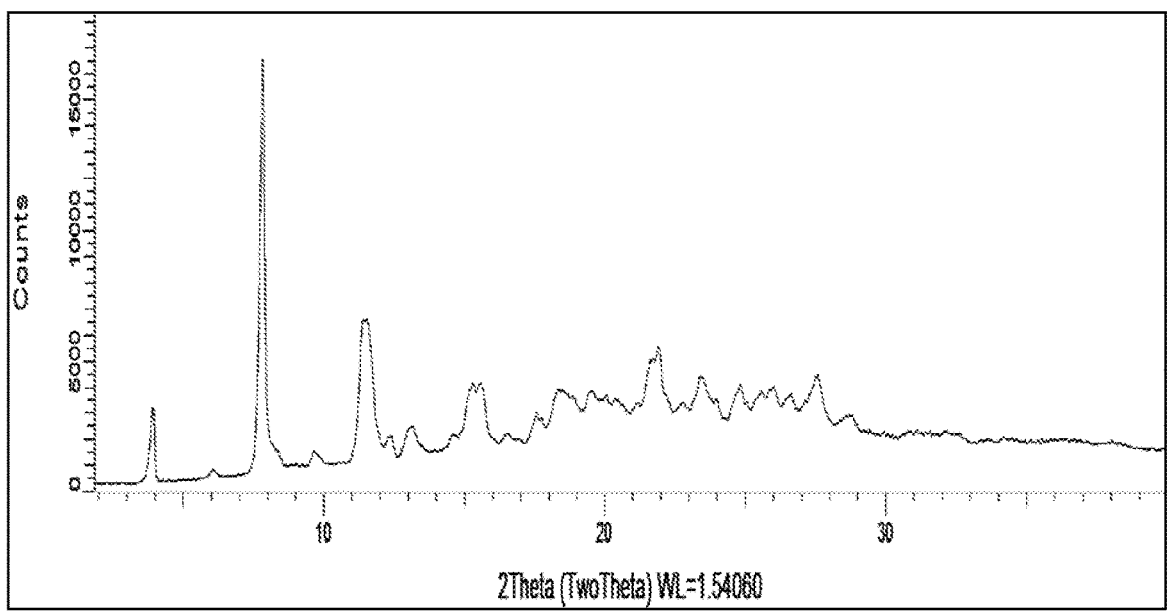

Figure 23: An X-ray powder diffractogram (XRPD) of Form T20 of Ivosidenib
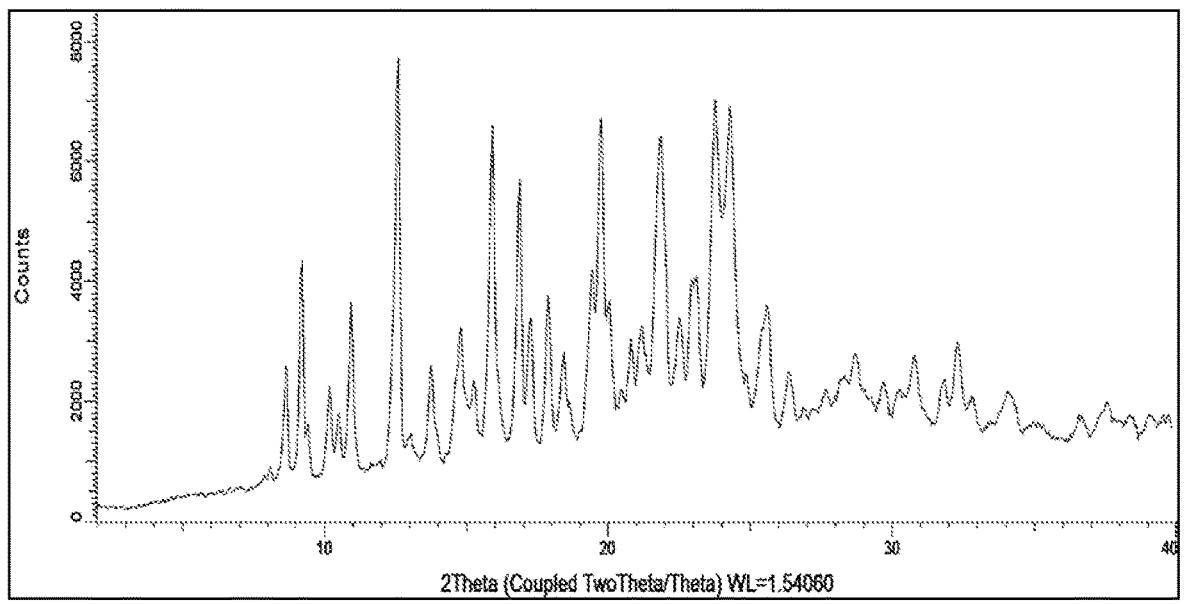
Figure 24: An X-ray powder diffractogram (XRPD) of Form T21 of Ivosidenib
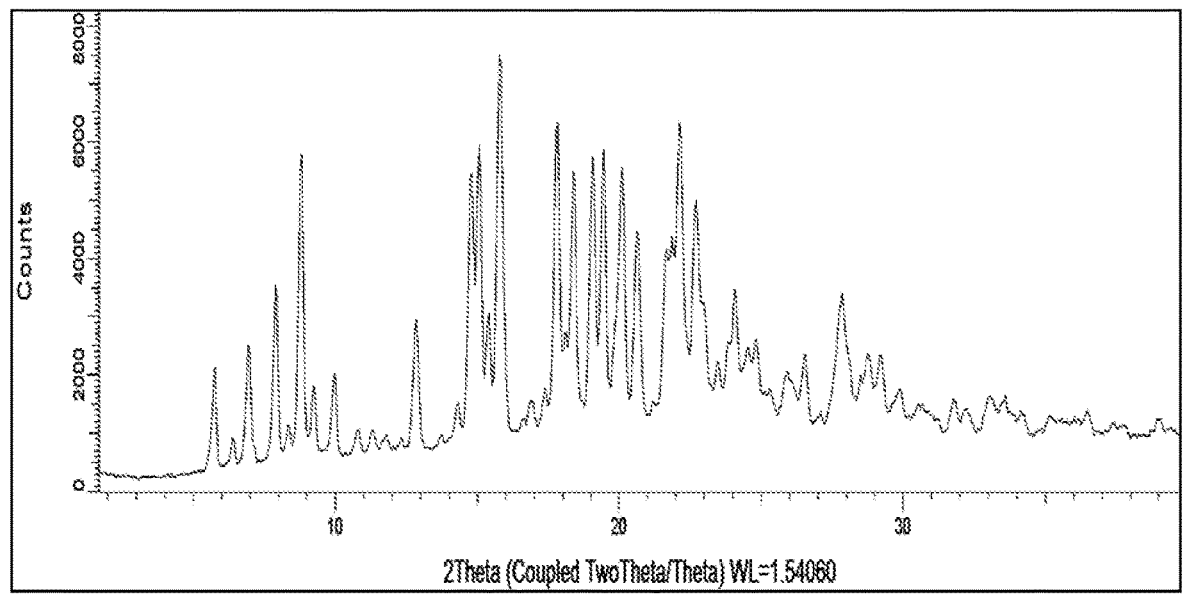

Figure 25: A DSC thermogram of Ivosidenib Form T11
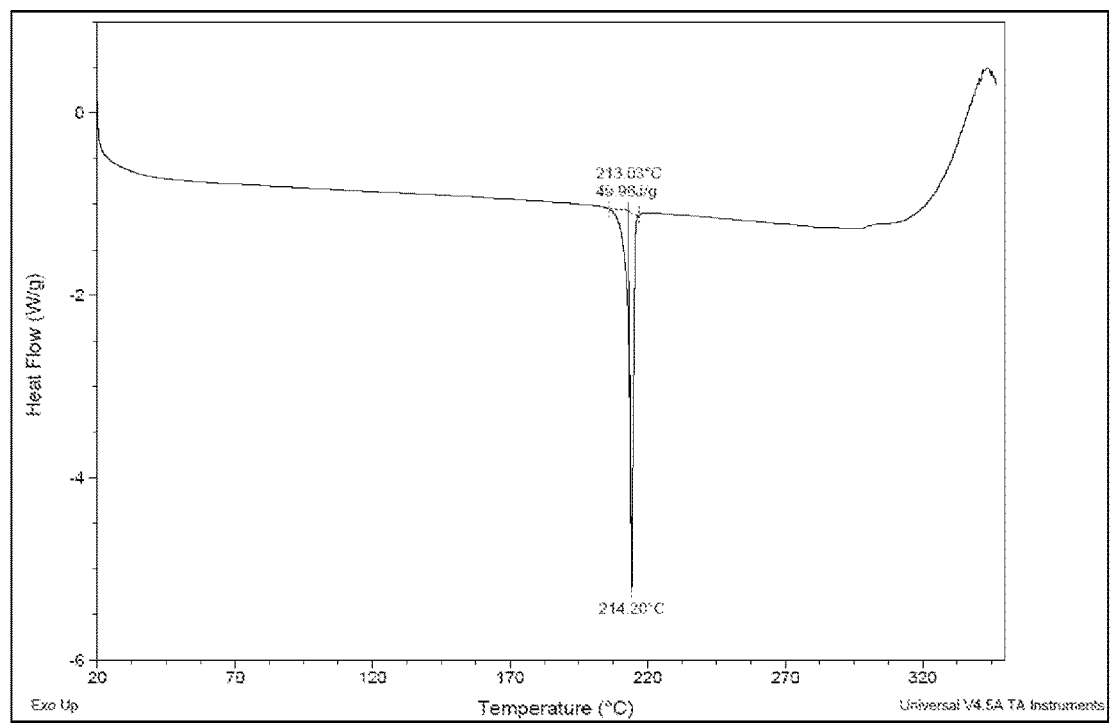
Figure 26: A TGA thermogram of Ivosidenib Form T11
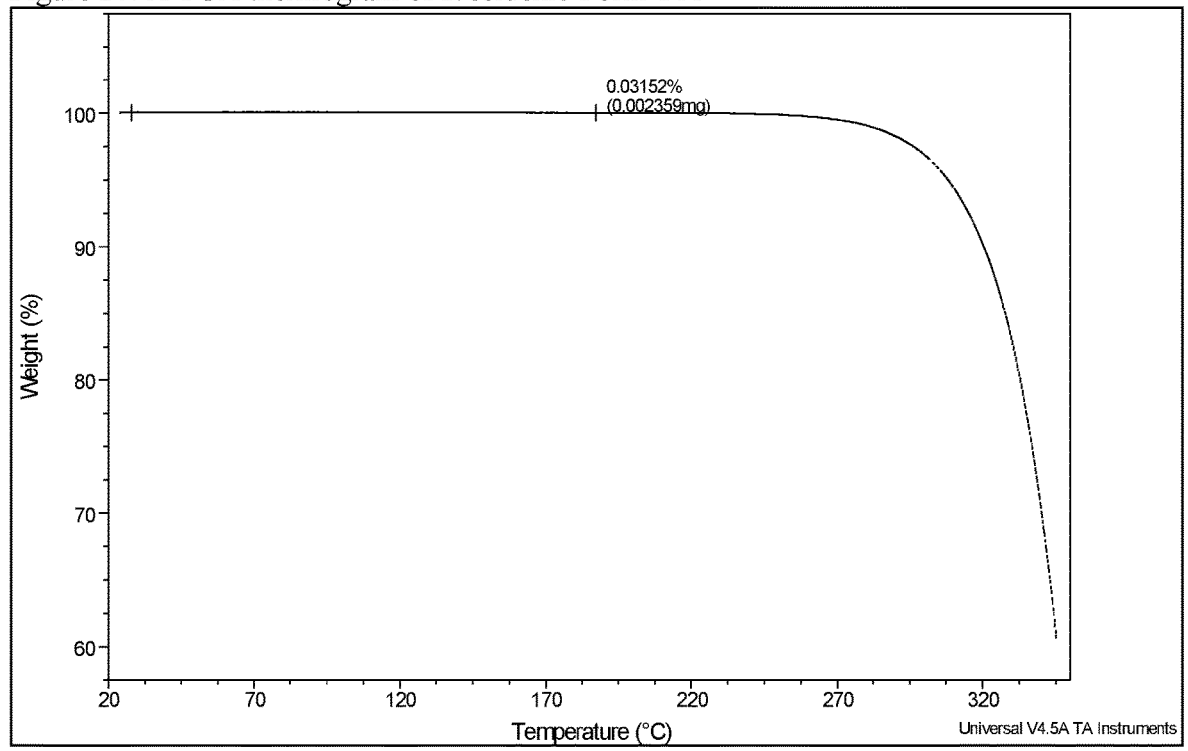

Figure 27: A solid state $^{13}$C-NMR spectrum of Form T11 of Ivosidenib
Figure 27A, -40-240ppm;
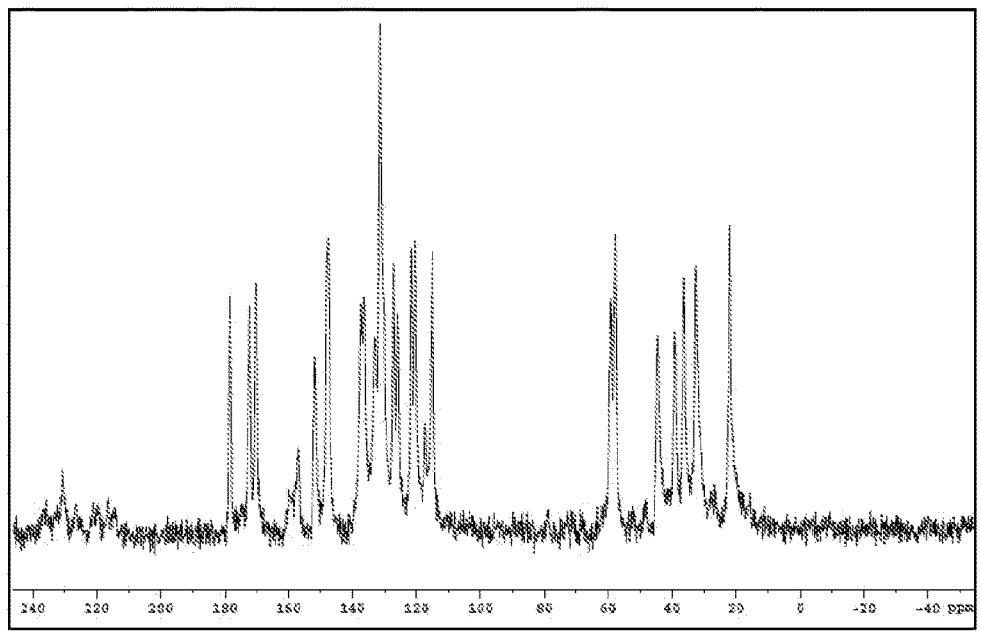
Figure 27B, 0-100ppm;
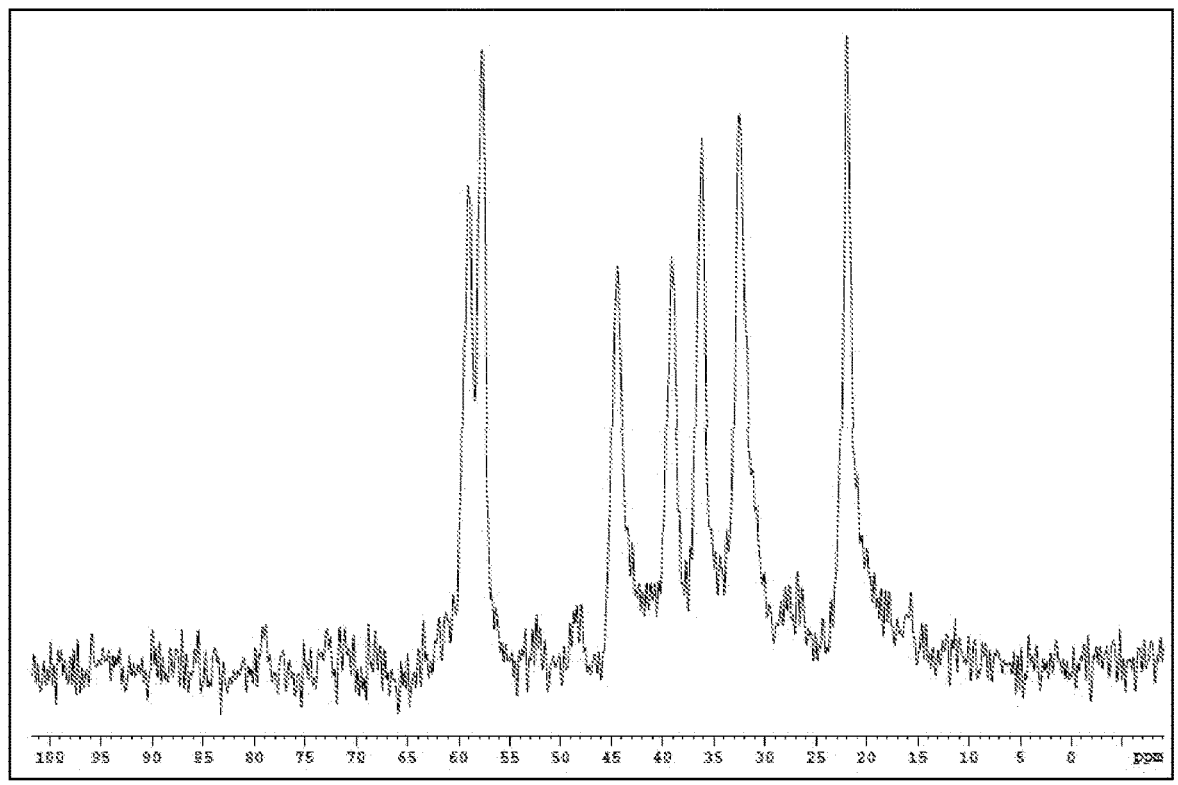

Figure 27C, 100-200ppm
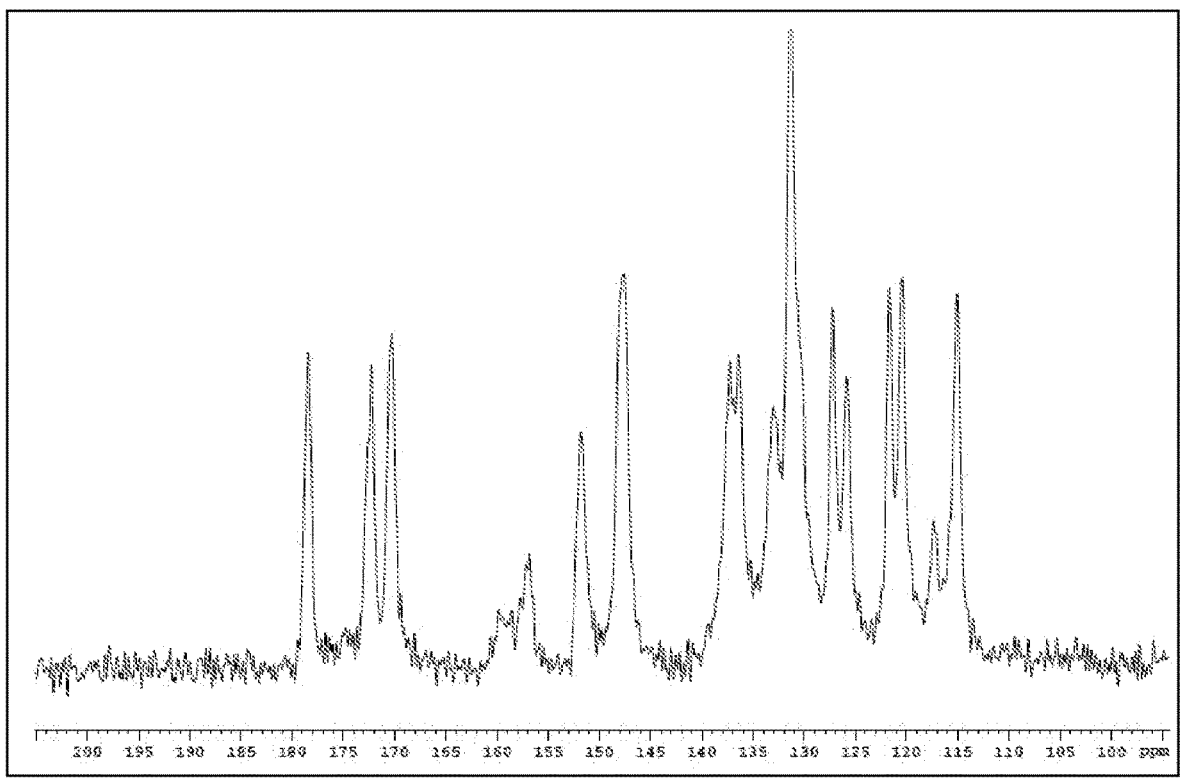

Figure 28: A solid state $^{13}$C-NMR spectrum of Form T14 of Ivosidenib
Figure 28A, -40-240ppm
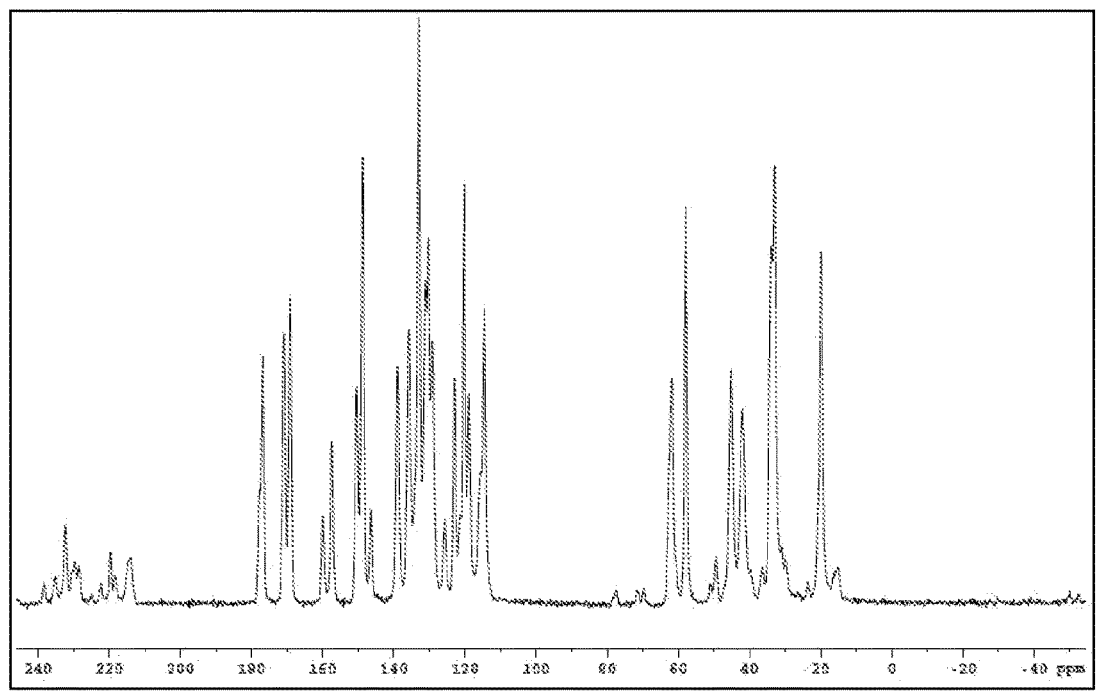
Figure 28B, 0-100ppm
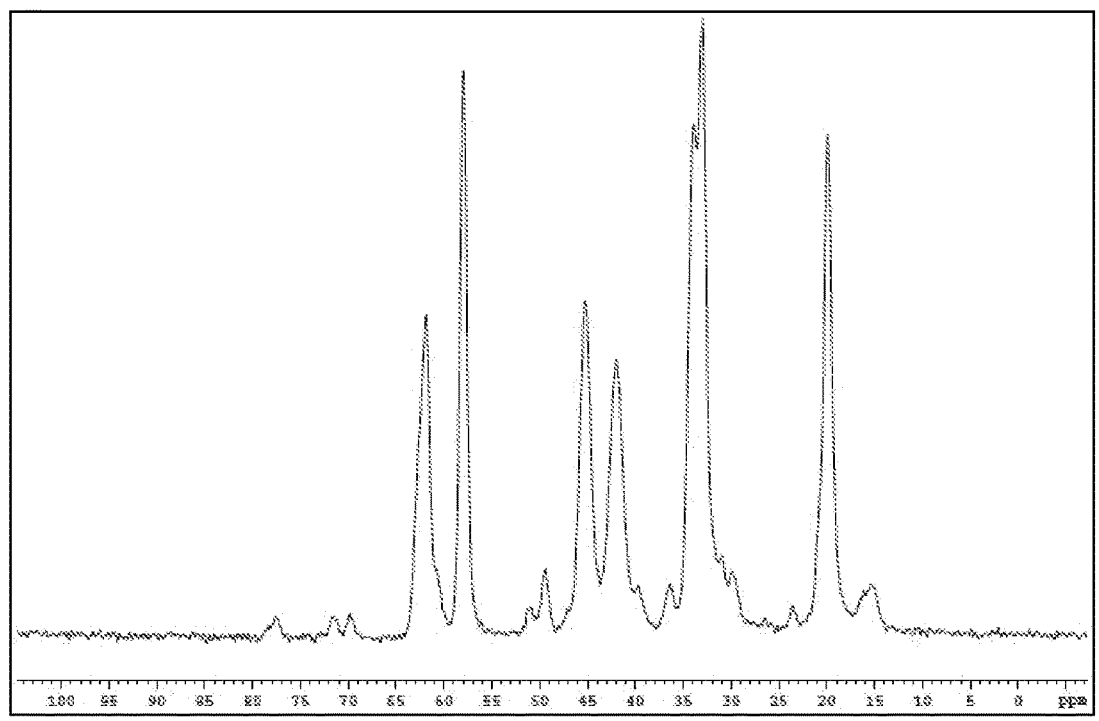

Figure 28C, 100-200ppm
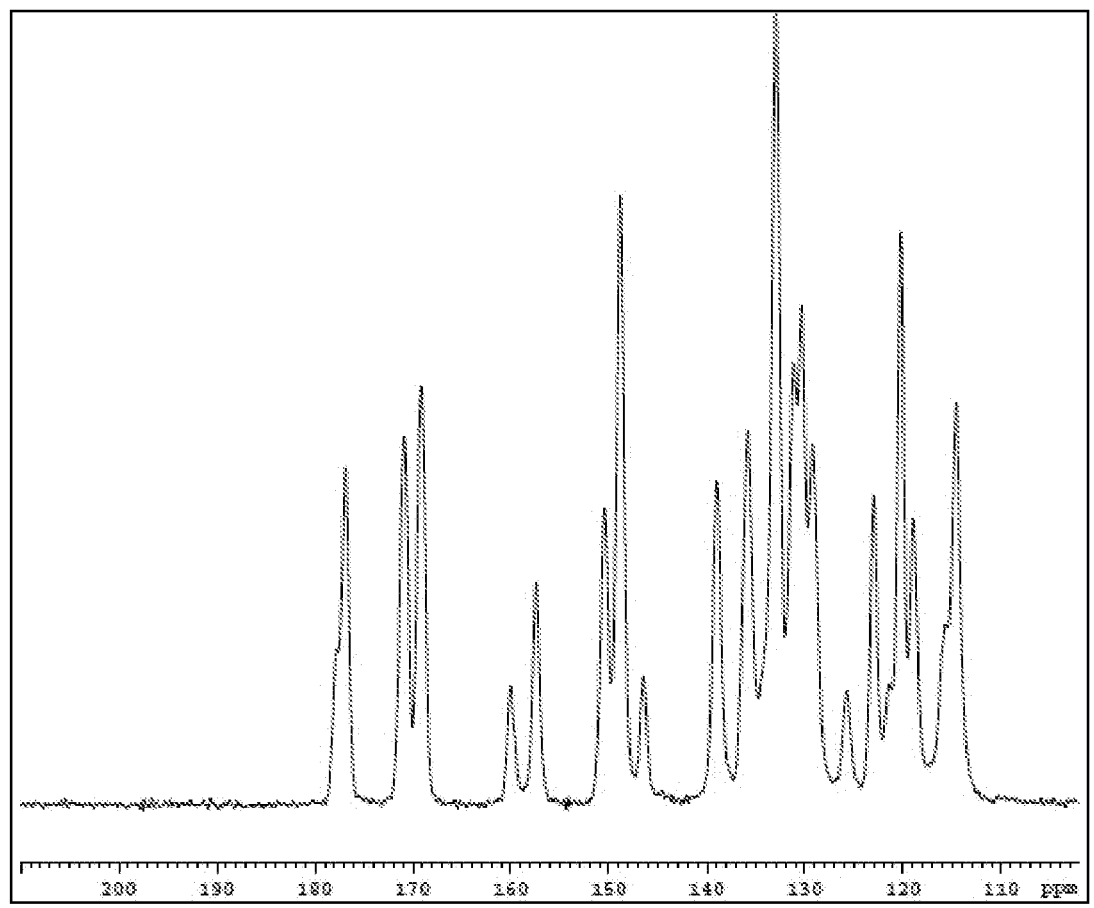

Figure 29: A solid state $^{13}$C-NMR spectrum of Form T15 of Ivosidenib
Figure 29A, -40-240ppm
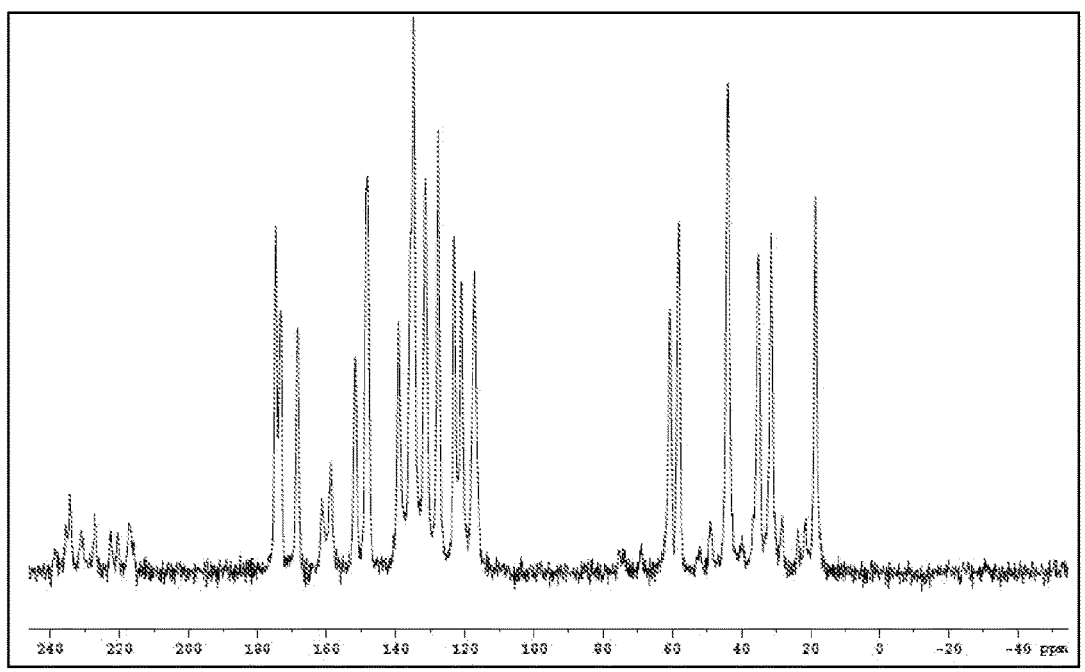
Figure 29B, 0-100ppm
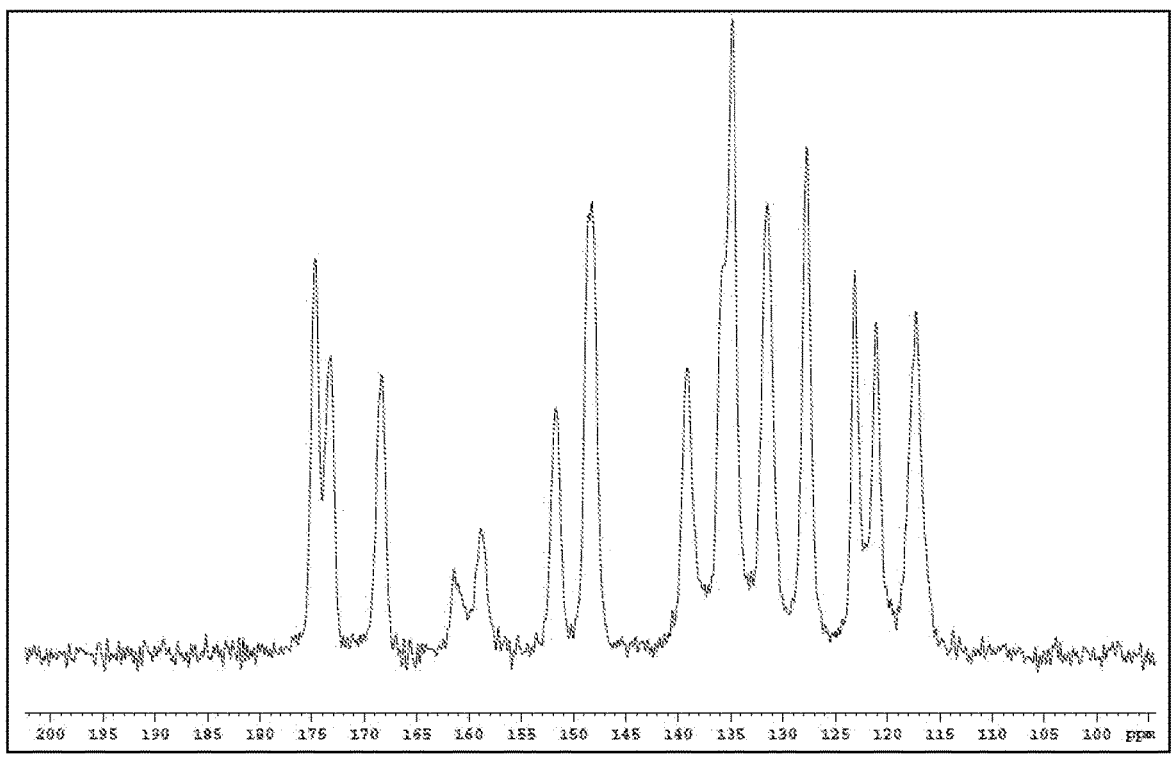

Figure 29C, 100-200ppm
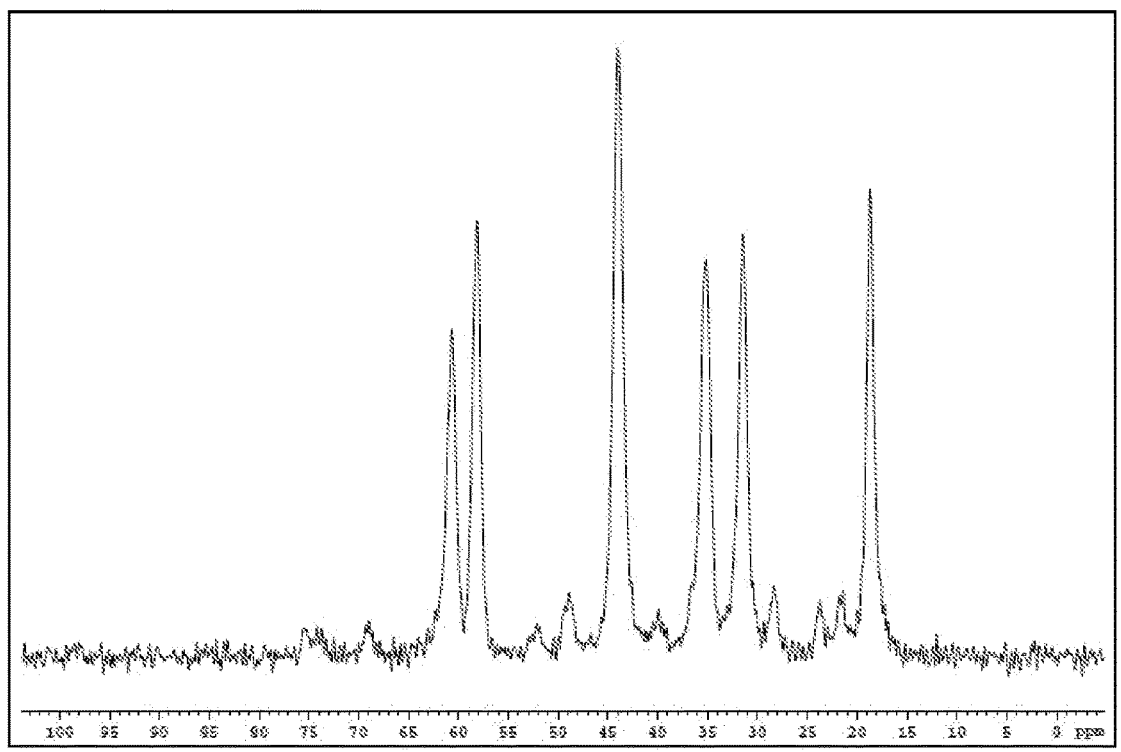

SOLID STATE FORMS OF IVOSIDENIB

CROSS REFERENCE TO RELATED APPLICATIONS

This application is a National Stage of, and claims priority to and the benefit of, International Patent Application No. PCT/US2018/062598 filed on Nov. 27, 2018, which, in turn, claims the benefit of, and priority to, IN Provisional Patent Application No. 201711042475, filed Nov. 27, 2017, IN Provisional Patent Application 201711044047, filed on Dec. 7, 2017, IN Provisional Patent Application No., 201811000614, filed Jan. 5, 2018, IN Provisional Patent Application No. 201811004740, filed Feb. 8, 2018, IN Provisional Patent Application No. 201811011325, filed Mar. 27, 2018, and IN Provisional Patent Application No. 201811040154, filed Oct. 24, 2018, the entire disclosures of each of which are incorporated by reference herein.

TECHNICAL FIELD

The present disclosure relates to solid state forms of Ivosidenib, processes for preparation thereof and pharmaceutical compositions thereof. The present disclosure further relates to processes for the preparation of Ivosidenib.

BACKGROUND

Ivosidenib has the chemical name (2S)—N-[(1S)-1-(2-chlorophenyl)-2-[(3,3-difluorocyclobutyl)amino]-2-oxoethyl]-1-(4-cyanopyridin-2-yl)-N-(5-fluoropyridin-3-yl)-5-oxopyrrolidine-2-carboxamide.

Ivosidenib has the following chemical structure:

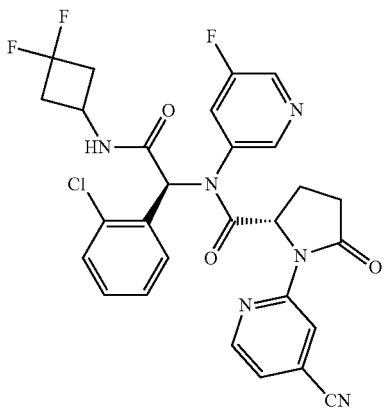 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

Ivosidenib is a small molecule inhibitor of isocitrate dehydrogenase 1 (IDH-1), which is mutated in several forms of cancer. Ivosidenib is being developed by Agios Pharmaceuticals for the treatment of cancer, particularly for the treatment of advanced hematologic malignancies, such as acute myelogenous leukemia (AML), cholangiocarcinoma, glioma, myelodysplastic syndromes, or solid tumors.

Ivosidenib has recently been approved by the FDA for treatment of adult patients with relapsed or refractory acute myeloid leukemia (AML) with a susceptible IDH1 mutation as detected by an FDA-approved test (1.1) and is marketed in the US under the tradename TIBSOVO®.

The FDA awarded orphan drug status for acute myeloid leukemia and cholangiocarcinoma.

Ivosidenib is disclosed in International Publication No. WO2013107291. Polymorphic forms of ivosidenib are disclosed in International Publication No. WO2015138839.

Polymorphism, the occurrence of different crystal forms, is a property of some molecules and molecular complexes. A single compound, like Ivosidenib, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}$C—) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms, and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability, which may offer better processing or handling characteristics, improved dissolution profile, or improved shelf-life.

For at least these reasons, there is a need for additional solid state forms (including solvated forms or salts) of Ivosidenib.

U.S. Pat. No. 9,474,779 discloses a process for preparing Ivosidenib. The described process includes chromatographic steps, has low yields and is not suitable for industrial scale.

For at least the above reasons, there is a need to have improved processes for preparing Ivosidenib, with increased efficiency and reasonable cost that can be used for an industrial scale.

SUMMARY

The present disclosure relates to solid state forms of Ivosidenib, processes for preparation thereof, and pharmaceutical compositions including these solid state forms.

The present disclosure also provides uses of the solid state forms of Ivosidenib or salts thereof for preparing other solid state forms of Ivosidenib, Ivosidenib salts and solid state forms thereof.

The present disclosure also provides uses of the solid state forms of Ivosidenib or salts thereof for preparing solid dispersions of Ivosidenib or Ivosidenib salts.

The present disclosure also provides solid state forms of Ivosidenib for uses in the preparation of other solid state forms of Ivosidenib or Ivosidenib salts and solid state forms thereof.

The present disclosure also provides solid state forms of Ivosidenib for use in the preparation of solid dispersions of Ivosidenib or Ivosidenib salts. The solid dispersion may include amorphous Ivosidenib and at least one pharmaceutically acceptable solid-dispersion carrier, in embodiments a polymer.

The present disclosure further provides processes for preparing other solid state forms of Ivosidenib, Ivosidenib salts and solid state forms thereof.

The present disclosure further provides processes for preparing solid dispersions of Ivosidenib or Ivosidenib salts from the disclosed solid state forms of Ivosidenib.

The present disclosure further encompasses processes for preparing solid dispersions of Ivosidenib including combining the described solid state form of Ivosidenib and at least one pharmaceutically acceptable solid-dispersion carrier. The present disclosure further encompasses processes for preparing solid dispersions of Ivosidenib including combining the described solid state form of Ivosidenib and one or more polymer(s).

In another embodiment, the present disclosure encompasses the described solid state forms of Ivosidenib for uses in the preparation of pharmaceutical compositions and/or formulations, optionally for the treatment of cancer, in embodiments for the treatment of advanced hematologic malignancies, such as acute myelogenous leukemia (AML), cholangiocarcinoma, glioma, myelodysplastic syndromes, or solid tumors.

In another embodiment, the present disclosure encompasses uses of the described solid state form of Ivosidenib for the preparation of pharmaceutical compositions and/or formulations.

The present disclosure further provides pharmaceutical compositions including the solid state form of Ivosidenib according to the present disclosure.

The present disclosure also provides solid dispersions of Ivosidenib including the solid state form of Ivosidenib according to the present disclosure. The present disclosure also provides pharmaceutical compositions including said solid dispersion(s).

The present disclosure also provides solid dispersions prepared by the described solid state forms of Ivosidenib.

The present disclosure also provides pharmaceutical compositions including a solid dispersion of Ivosidenib prepared by the described solid state forms of Ivosidenib.

In yet another embodiment, the present disclosure encompasses pharmaceutical formulations including the described solid state forms of Ivosidenib and at least one pharmaceutically acceptable excipient.

The present disclosure encompasses processes to prepare said pharmaceutical formulations of Ivosidenib including combining the described solid state form and at least one pharmaceutically acceptable excipient.

The solid state forms defined herein as well as the pharmaceutical compositions or formulations of the solid state form of Ivosidenib can be used as medicaments, in embodiments for the treatment of cancer, such as for the treatment of advanced hematologic malignancies, including acute myelogenous leukemia (AML), cholangiocarcinoma, glioma, myelodysplastic syndromes, or solid tumors.

The present disclosure also provides methods of treating cancer, in embodiments for the treatment of advanced hematologic malignancies, such as acute myelogenous leukemia (AML), cholangiocarcinoma, glioma, myelodysplastic syndromes, or solid tumors, including administering a therapeutically effective amount of the solid state form of Ivosidenib of the present disclosure, or at least one of the herein described pharmaceutical compositions or formulations, to a subject suffering from cancer, in embodiments for the treatment of advanced hematologic malignancies, such as acute myelogenous leukemia (AML), cholangiocarcinoma, glioma, myelodysplastic syndromes and solid tumors.

The present disclosure also provides uses of the solid state forms of Ivosidenib of the present disclosure, or at least one of the above pharmaceutical compositions or formulations for the manufacture of medicaments for treating cancer, in embodiments for the treatment of advanced hematologic malignancies, such as acute myelogenous leukemia (AML), cholangiocarcinoma, glioma, myelodysplastic syndromes, or solid tumors.

The present disclosure further relates to processes for preparing Ivosidenib or Ivosidenib salts.

The present disclosure relates to an improved process for preparing Ivosidenib, which is suitable for industrial scale, avoids hazardous and unstable intermediates, has high yields and leads to a chemical and enantiomeric pure product.

BRIEF DESCRIPTION OF THE FIGURES

FIG. 1 shows an X-ray powder diffractogram (XRPD) of amorphous Ivosidenib.
FIG. 2 shows an XRPD of Form T1 of Ivosidenib.
FIG. 3 shows an XRPD of Form T2 of Ivosidenib.
FIG. 4 shows an XRPD of Form T3 of Ivosidenib.
FIG. 5 shows an XRPD of Form T4 of Ivosidenib.
FIG. 6 shows an XRPD of Form T5 of Ivosidenib.
FIG. 7 shows an XRPD of Form T6 of Ivosidenib.
FIG. 8 shows an XRPD of Form T7 of Ivosidenib.
FIG. 9 shows an XRPD of Form T8 of Ivosidenib.
FIG. 10 shows an XRPD of Form T9 of Ivosidenib.
FIG. 11 shows an XRPD of Form T10 of Ivosidenib.
FIG. 12 shows an XRPD of Form T11 of Ivosidenib.
FIG. 13 shows an XRPD of Form T12 of Ivosidenib.
FIG. 14 shows an XRPD of Form T13 of Ivosidenib.
FIG. 15 shows an XRPD of Form T14 of Ivosidenib.
FIG. 16 shows thermogravimetric analysis (TGA) thermogram spectrum of Form T14 of Ivosidenib.
FIG. 17 shows an XRPD of Form T15 of Ivosidenib.
FIG. 18 shows thermogravimetric analysis (TGA) thermogram spectrum of Form T15 of Ivosidenib.
FIG. 19 shows an XRPD of Form T16 of Ivosidenib.
FIG. 20 shows an XRPD of Form T17 of Ivosidenib.
FIG. 21 shows an XRPD of Form T18 of Ivosidenib.
FIG. 22 shows an XRPD of Form T19 of Ivosidenib.
FIG. 23 shows an XRPD of Form T20 of Ivosidenib.
FIG. 24 shows an XRPD of Form T21 of Ivosidenib.
FIG. 25 shows a Differential Scanning Calorimetry (DSC) thermogram of Form T11.
FIG. 26 shows a thermogravimetric analysis (TGA) spectrum of Form T11.
FIG. 27 shows a solid state $^{13}$C-NMR spectrum of Form T11 of Ivosidenib (FIG. 27A, −40-240 ppm; FIG. 27B, 0-100 ppm; FIG. 27C, 100-200 ppm).
FIG. 28 shows a solid state $^{13}$C-NMR spectrum of Form T14 of Ivosidenib (FIG. 28A, −40-240 ppm; FIG. 28B, 0-100 ppm; FIG. 28C, 100-200 ppm).

FIG. 29 shows a solid state $^{13}$C-NMR spectrum of Form T15 of Ivosidenib (FIG. 29A, −40-240 ppm; FIG. 29B, 0-100 ppm; FIG. 29C, 100-200 ppm).

DETAILED DESCRIPTION OF THE INVENTION

The present disclosure relates to solid state forms of Ivosidenib, processes for preparation thereof and pharmaceutical compositions including these solid state forms. The disclosure also relates to the conversion of the described solid state forms of Ivosidenib to other solid state forms of Ivosidenib, Ivosidenib salts and solid state forms thereof.

The solid state forms of Ivosidenib according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Ivosidenib referred to herein as being characterized by graphical data "as depicted in" a Figure will thus be understood to include any crystal forms of the Ivosidenib, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or 0% of any other forms of the subject compound as measured, for example, by XRPD. Thus, the solid state form of Ivosidenib described herein as substantially free of any other solid state forms would be understood to contain greater than about 80% (w/w), greater than about 90% (w/w), greater than about 95% (w/w), greater than about 98% (w/w), greater than about 99% (w/w), or 100% of the subject solid state form of Ivosidenib. Accordingly, in some embodiments of the disclosure, the described solid state forms of Ivosidenib may contain from about 1% to about 20% (w/w), from about 5% to about 20% (w/w), or from about 5% to about 10% (w/w) of one or more other solid state forms of the same Ivosidenib.

As used herein, unless stated otherwise, XRPD peaks reported herein are optionally measured using CuK$_\alpha$ radiation, λ=1.5418 Å.

As used herein, the term "isolated" in reference to solid state forms of Ivosidenib of the present disclosure corresponds to solid state form of Ivosidenib that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, about 10 to about 18 hours, or about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

As used herein, and unless stated otherwise, the term "anhydrous" in relation to crystalline Ivosidenib relates to crystalline Ivosidenib which does not include any crystalline water (or other solvents) in a defined, stoichiometric amount within the crystal. Moreover, an "anhydrous" form does not contain more than about 1% (w/w) of either water or organic solvents as measured for example by TGA.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

As used herein the term non-hygroscopic in relation to crystalline Ivosidenib refers to less than about 0.2% (w/w) absorption of water at about 25° C. and about 80% relative humidity (RH) by the crystalline Ivosidenib as determined for example by TGA. Water can be, for example, atmospheric water.

As used herein, the term "reduced pressure" refers to a pressure of about 10 mbar to about 50 mbar.

The present disclosure comprises an amorphous form of Ivosidenib. The amorphous form of Ivosidenib can be characterized by an XRPD pattern as depicted in FIG. 1.

The present disclosure further comprises a crystalline form of Ivosidenib designated as Form T1. The crystalline Form T1 of Ivosidenib can be characterized by data selected from one or more of the following: an XRPD pattern having peaks at 6.4, 14.4, 16.1, 18.9, 25.5 and 26.9 deg-2-theta±0.2 deg 2-theta; an XRPD pattern as depicted in FIG. 2; and combinations of these data. Crystalline Form T1 of Ivosidenib may be further characterized by the XRPD pattern having peaks at 6.4, 14.4, 16.1, 18.9, 25.5 and 26.9 deg-2-theta±0.2 deg 2-theta, and also having one, two, three, four or five additional peaks selected from 12.9, 17.5, 20.6, 21.8, 22.7 and 24.4 deg-2-theta±0.2 deg 2-theta.

Crystalline Form T1 of Ivosidenib may be characterized by each of the above characteristics alone/or by all possible combinations, e.g. by XRPD pattern having peaks at 6.4, 14.4, 16.1, 18.9, 25.5 and 26.9 deg-2-theta±0.2 deg 2-theta and an XRPD pattern as depicted in FIG. 2. Crystalline Form T1 may be a solvate. Crystalline Form T1 may be an anisole solvate.

The present disclosure further comprises a crystalline form of Ivosidenib designated as Form T2. The crystalline Form T2 of Ivosidenib can be characterized by data selected from one or more of the following: an XRPD pattern having peaks at 8.2, 9.2, 10.1, 16.6, 21.3 and 23.7 deg-2-theta±0.2 deg 2-theta; an XRPD pattern as depicted in FIG. 3; and combinations of these data. Crystalline Form T2 of Ivosidenib may be further characterized by the XRPD pattern having peaks at 8.2, 9.2, 10.1, 16.6, 21.3 and 23.7 deg 2-theta±0.2 deg 2-theta, and also having one, two, three, four or five additional peaks selected from 13.0, 22.2, 25.3, 28.5 and 30.8 deg 2-theta±0.2 deg 2-theta.

Crystalline Form T2 of Ivosidenib may be characterized by each of the above characteristics alone/or by all possible combinations, e.g. by XRPD pattern having peaks at 8.2, 9.2, 10.1, 16.6, 21.3 and 23.7 deg-2-theta±0.2 deg 2-theta and an XRPD pattern as depicted in FIG. 3. Crystalline Form T2 may be a solvate. Crystalline Form T2 may be an isoamyl alcohol solvate.

The present disclosure further comprises a crystalline form of Ivosidenib designated as Form T3. The crystalline Form T3 of Ivosidenib can be characterized by data selected from one or more of the following: an XRPD pattern having peaks at 7.6, 8.4, 15.2, 15.9, 21.5 and 23.9 deg-2-theta±0.2 deg 2-theta; an XRPD pattern as depicted in FIG. 4; and combinations of these data. Crystalline Form T3 of Ivosidenib may be further characterized by the XRPD pattern having peaks at 7.6, 8.4, 15.2, 15.9, 21.5 and 23.9 deg-2-theta±0.2 deg 2-theta, and also having one, two, three, four or five additional peaks selected from 9.5, 16.8, 18.0, 22.4 and 26.7 deg-2-theta±0.2 deg 2-theta.

Crystalline Form T3 of Ivosidenib may be characterized by each of the above characteristics alone/or by all possible combinations, e.g. by XRPD pattern having peaks at 7.6, 8.4, 15.2, 15.9, 21.5 and 23.9 deg-2-theta±0.2 deg 2-theta and an XRPD pattern as depicted in FIG. 4. Crystalline Form T3 may be a solvate. Crystalline Form T3 may be a propyl acetate solvate.

The present disclosure further comprises a crystalline form of Ivosidenib designated as Form T4. The crystalline Form T4 of Ivosidenib can be characterized by data selected from one or more of the following: an XRPD pattern having peaks at 6.6, 12.1, 14.9, 17.6 and 21.0 deg-2-theta±0.2 deg 2-theta; an XRPD pattern as depicted in FIG. 5; and combinations of these data. Crystalline Form T4 of Ivosidenib may be further characterized by the XRPD pattern having peaks at 6.6, 12.1, 14.9, 17.6 and 21.0 deg-2-theta±0.2 deg 2-theta, and also having one, two, three, four or five additional peaks selected from 14.2, 19.1, 22.4, 23.0 and 25.4 deg-2-theta±0.2 deg 2-theta.

Crystalline Form T4 of Ivosidenib may be characterized by each of the above characteristics alone/or by all possible combinations, e.g. by XRPD pattern having peaks at 6.6, 12.1, 14.9, 17.6 and 21.0 deg-2-theta±0.2 deg 2-theta and an XRPD pattern as depicted in FIG. 5. Crystalline Form T4 may be a solvate. Crystalline Form T4 may be a methylacetate solvate.

The present disclosure further comprises a crystalline form of Ivosidenib designated as Form T5. The crystalline Form T5 of Ivosidenib can be characterized by data selected from one or more of the following: an XRPD pattern having peaks at 6.4, 11.8, 14.1, 14.5, 17.4 and 22.8 deg-2-theta±0.2 deg 2-theta; an XRPD pattern as depicted in FIG. 6; and combinations of these data. Crystalline Form T5 of Ivosidenib may be further characterized by the XRPD pattern having peaks at 6.4, 11.8, 14.1, 14.5, 17.4 and 22.8 deg-2-theta±0.2 deg 2-theta, and also having one, two, three, four or five additional peaks selected from 20.0, 21.0, 23.8, and 25.8 deg-2-theta±0.2 deg 2-theta.

Crystalline Form T5 of Ivosidenib may be characterized by each of the above characteristics alone/or by all possible combinations, e.g. by XRPD pattern having peaks at 6.4, 11.8, 14.1, 14.5, 17.4 and 22.8 deg-2-theta±0.2 deg 2-theta and an XRPD pattern as depicted in FIG. 6. Crystalline Form T5 may be a solvate. Crystalline Form T5 may be an ethylacetate solvate.

The present disclosure further comprises a crystalline form of Ivosidenib designated as Form T6. The crystalline Form T6 of Ivosidenib can be characterized by data selected from one or more of the following: an XRPD pattern having peaks at 3.5, 7.2, 8.9, 10.8, 14.5, 18.0 and 23.3 deg-2-theta±0.2 deg 2-theta; an XRPD pattern as depicted in FIG. 7; and combinations of these data. Crystalline Form T6 of Ivosidenib may be further characterized by the XRPD pattern having peaks at 3.5, 7.2, 8.9, 10.8, 14.5, 18.0 and 23.3 deg-2-theta±0.2 deg 2-theta, and also having one, two, three, four or five additional peaks selected from 16.0, 17.4, 20.7, 21.1, 25.5 and 29.4 deg-2-theta±0.2 deg 2-theta.

Crystalline Form T6 of Ivosidenib may be characterized by each of the above characteristics alone/or by all possible combinations, e.g. by XRPD pattern having peaks at 3.5, 7.2, 8.9, 10.8, 14.5, 18.0 and 23.3 deg-2-theta±0.2 deg 2-theta and an XRPD pattern as depicted in FIG. 7. Crystalline Form T6 may be a solvate. Crystalline Form T6 may be a DMSO solvate.

The present disclosure further comprises a crystalline form of Ivosidenib designated as Form T7. The crystalline Form T7 of Ivosidenib can be characterized by data selected from one or more of the following: an XRPD pattern having peaks at 8.6, 9.8, 10.5, 12.1, 19.5 and 21.9 deg-2-theta±0.2 deg 2-theta; an XRPD pattern as depicted in FIG. 8; and combinations of these data. Crystalline Form T6 of Ivosidenib may be further characterized by the XRPD pattern having peaks at 8.6, 9.8, 10.5, 12.1, 19.5 and 21.9 deg-2-theta±0.2 deg 2-theta, and also having one, two, three, four or five additional peaks selected from 13.5, 17.1, 20.6 and 22.9 deg-2-theta±0.2 deg 2-theta.

Crystalline Form T7 of Ivosidenib may be characterized by each of the above characteristics alone/or by all possible combinations, e.g. by XRPD pattern having peaks at 8.6, 9.8, 10.5, 12.1, 19.5 and 21.9 deg-2-theta±0.2 deg 2-theta and an XRPD pattern as depicted in FIG. 8. Crystalline Form T7 may be a solvate. Crystalline Form T7 may be a 1,3-dioxolane solvate solvate.

The present disclosure further comprises a crystalline form of Ivosidenib designated as Form T8. The crystalline Form T8 of Ivosidenib can be characterized by data selected from one or more of the following: an XRPD pattern having peaks at 7.8, 11.3, 14.2, 17.0, 17.5 and 20.1 deg-2-theta±0.2 deg 2-theta; an XRPD pattern as depicted in FIG. 9; and combinations of these data. Crystalline Form T8 of Ivosidenib may be further characterized by the XRPD pattern having peaks at 7.8, 11.3, 14.2, 17.0, 17.5 and 20.1 deg-2-theta±0.2 deg 2-theta, and also having one, two, three, four or five additional peaks selected from 8.2, 10.3, 15.7, 20.5, 21.6 and 24.5 deg-2-theta±0.2 deg 2-theta.

Crystalline Form T8 of Ivosidenib may be characterized by each of the above characteristics alone/or by all possible combinations, e.g. by XRPD pattern having peaks at 7.8, 11.3, 14.2, 17.0, 17.5 and 20.1 deg-2-theta±0.2 deg 2-theta and an XRPD pattern as depicted in FIG. 9. Crystalline Form T8 may be a solvate. Crystalline Form T8 may be ap-xylene solvate.

The present disclosure further comprises a crystalline form of Ivosidenib designated as Form T9. The crystalline Form T9 of Ivosidenib can be characterized by data selected from one or more of the following: an XRPD pattern having peaks at 7.9, 22.1, 22.7, 23.9, 27.9 and 29.2 deg-2-theta±0.2 deg 2-theta; an XRPD pattern as depicted in FIG. 10; and combinations of these data. Crystalline Form T9 of Ivosidenib may be further characterized by the XRPD pattern having peaks at 7.9, 22.1, 22.7, 23.9, 27.9 and 29.2 deg-2-theta±0.2 deg 2-theta, and also having one, two, three, four or five additional peaks selected from 10.8, 20.7, 21.3, 21.6, 26.2 and 26.6 deg-2-theta±0.2 deg 2-theta.

Crystalline Form T9 of Ivosidenib may be characterized by each of the above characteristics alone/or by all possible combinations, e.g. by XRPD pattern having peaks at 7.9, 22.1, 22.7, 23.9, 27.9 and 29.2 deg-2-theta±0.2 deg 2-theta and an XRPD pattern as depicted in FIG. 10. Crystalline Form T9 may be a solvate. Crystalline Form T9 may be a 1,2-dimethoxyethane solvate.

The present disclosure further comprises a crystalline form of Ivosidenib designated as Form T10. The crystalline Form T10 of Ivosidenib can be characterized by data selected from one or more of the following: an XRPD pattern having peaks at 7.2, 11.6, 16.2, 19.9, 23.5 and 27.0 deg-2-theta±0.2 deg 2-theta; an XRPD pattern as depicted in FIG. 11; and combinations of these data. Crystalline Form T10 of Ivosidenib may be further characterized by the XRPD pattern having peaks at 7.2, 11.6, 16.2, 19.9, 23.5 and 27.0 deg-2-theta±0.2 deg 2-theta, and also having one, two, three, four or five additional peaks selected from 6.3, 13.0, 14.4, 17.3 and 18.9 deg-2-theta±0.2 deg 2-theta.

Crystalline Form T10 of Ivosidenib may be characterized by each of the above characteristics alone/or by all possible combinations, e.g. by XRPD pattern having peaks at 7.2, 11.6, 16.2, 19.9, 23.5 and 27.0 deg-2-theta±0.2 deg 2-theta and an XRPD pattern as depicted in FIG. 11. Crystalline Form T10 may be a solvate. Crystalline Form T10 may be a chlorobenzene solvate.

The present disclosure further comprises a crystalline form of Ivosidenib designated as Form T11. The crystalline Form T11 of Ivosidenib can be characterized by data selected from one or more of the following: an XRPD pattern having peaks at 14.3, 15.9, 21.2, 22.7 and 23.8 deg-2-theta±0.2 deg 2-theta; an XRPD pattern as depicted in FIG. 12; and combinations of these data. Crystalline Form T11 of Ivosidenib may alternatively or additionally be characterized by data selected from one or more of the following: a solid state $^{13}$C-NMR spectrum with peaks at 178.4, 172.3, 151.8, 147.7 and 131.3 ppm±0.2 ppm; or by a solid state $^{13}$C-NMR spectrum having the following chemical shift absolute differences from a peak at 57.8 ppm±2 ppm of 120.6, 114.5, 94.0, 89.9 and 73.5 ppm±0.1 ppm; or by a solid state $^{13}$C NMR spectrum having chemical shift difference from a peak at 178.4 ppm±1 ppm of 120.6 ppm±0.1 ppm; or by a solid state $^{13}$C-NMR spectrum substantially as depicted in FIG. 27; or combinations of these data.

Crystalline Form T11 of Ivosidenib may be further characterized by the XRPD pattern having peaks at 14.3, 15.9, 21.2, 22.7 and 23.8 deg-2-theta±0.2 deg 2-theta, and also having one, two, three, four or five additional peaks selected from 8.6, 17.4, 19.3, 26.2 and 29.0 deg-2-theta±0.2 deg 2-theta. Crystalline Form T11 of Ivosidenib may alternatively or additionally be characterized by data selected from one or more of the following: a DSC thermogram as depicted in FIG. 25; a TGA thermogram as depicted in FIG. 26. Crystalline Form T11 shows a melting endothermic peak at about 214.2° C. according to DSC thermogram. Further, crystalline Form T11 shows weight loss of less than 1% of the weight of the sample in a TGA thermogram upon heating up to 300° C. Preferably, Form T11 shows weight loss of less than 0.05% of the weight of the sample in a TGA thermogram. Form T11 shows weight loss of about 0.03% of the weight of the sample in a TGA thermogram.

Crystalline Form T11 of Ivosidenib may be characterized by each of the above characteristics alone/or by all possible combinations, e.g. by XRPD pattern having peaks at 14.3, 15.9, 21.2, 22.7 and 23.8 deg-2-theta±0.2 deg 2-theta and an XRPD pattern as depicted in FIG. 12. Crystalline Form T11 is anhydrous. The water content in crystalline Form T11 may be between 0.0% to 1.0%, between 0.0% to 0.5%, between 0.0% to 0.3%, as determined by TGA and Karl Fischer titration method. Preferably, the water content of crystalline Form T11 is less than 1% as measured by Karl-Fischer titration method.

Crystalline Form T11 of Ivosidenib is stable and shows a very good flowability.

The present disclosure further comprises a crystalline form of Ivosidenib designated as Form T12. The crystalline Form T12 of Ivosidenib can be characterized by data selected from one or more of the following: an XRPD pattern having peaks at 6.3, 14.2, 20.9, 25.0 and 29.8 deg-2-theta±0.2 deg 2-theta; an XRPD pattern as depicted in FIG. 13; and combinations of these data. Crystalline Form T12 of Ivosidenib may be further characterized by the XRPD pattern having peaks at 6.3, 14.2, 20.9, 25.0 and 29.8 deg-2-theta±0.2 deg 2-theta, and also having one, two, three, four or five additional peaks selected from 11.6, 15.5, 17.0 and 27.7 deg-2-theta±0.2 deg 2-theta.

Crystalline Form T12 of Ivosidenib may be characterized by each of the above characteristics alone/or by all possible combinations, e.g. by XRPD pattern having peaks at 6.3, 14.2, 20.9, 25.0 and 29.8 deg-2-theta±0.2 deg 2-theta and an XRPD pattern as depicted in FIG. 13. Crystalline Form T12 may be a solvate. Crystalline Form T12 may be a isopropyl acetate solvate.

The present disclosure further comprises a crystalline form of Ivosidenib designated as Form T13. The crystalline Form T13 of Ivosidenib can be characterized by data selected from one or more of the following: an XRPD pattern having peaks at 13.0, 14.7, 16.7, 17.8, 19.7 and 24.2 deg-2-theta±0.2 deg 2-theta; an XRPD pattern as depicted in FIG. 14; and combinations of these data. Crystalline Form T13 of Ivosidenib may be further characterized by the XRPD pattern having peaks at 13.0, 14.7, 16.7, 17.8, 19.7 and 24.2 deg-2-theta±0.2 deg 2-theta, and also having one, two, three, four or five additional peaks selected from 7.5, 8.3, 15.2, 20.8 and 21.6 deg-2-theta±0.2 deg 2-theta.

Crystalline Form T13 of Ivosidenib may be characterized by each of the above characteristics alone/or by all possible combinations, e.g. by XRPD pattern having peaks at 13.0, 14.7, 16.7, 17.8, 19.7 and 24.2 deg-2-theta±0.2 deg 2-theta and an XRPD pattern as depicted in FIG. 14. Crystalline Form T13 may be a solvate. Crystalline Form T13 may be an isobutyl acetate solvate.

The present disclosure further comprises a crystalline form of Ivosidenib designated as Form T14. The crystalline Form T14 of Ivosidenib can be characterized by data selected from one or more of the following: an XRPD pattern having peaks at 10.3, 12.4, 17.8, 20.0, 29.2 and 31.7 deg-2-theta±0.2 deg 2-theta; an XRPD pattern as depicted in FIG. 15; and combinations of these data. Crystalline Form T14 of Ivosidenib may alternatively or additionally be characterized by data selected from one or more of the following: a solid state $^{13}$C-NMR spectrum with peaks at 176.9, 170.9, 169.1, 148.8 and 133.0 ppm±0.2 ppm; or by a solid state $^{13}$C-NMR spectrum having the following chemical shift absolute differences from a peak at 58.0 ppm±2 ppm of 118.9, 112.9, 111.1, 90.8 and 75.0 ppm±0.1 ppm; or by a solid state $^{13}$C NMR spectrum having chemical shift difference from a peak at 176.9 ppm±1 ppm of 118.7 ppm±0.1 ppm; or by a solid state $^{13}$C-NMR spectrum substantially as depicted in FIG. 28; or combinations of these data.

Crystalline Form T14 of Ivosidenib may be further characterized by the XRPD pattern having peaks at 10.3, 12.4, 17.8, 20.0, 29.2 and 31.7 and 24.2 deg-2-theta±0.2 deg 2-theta, and also having one, two, three, four or five additional peaks selected from 14.5, 15.9, 21.2, 22.7 and 23.2 deg-2-theta±0.2 deg 2-theta. Crystalline Form T14 of Ivosidenib may be further characterized by the XRPD pattern having one, two, three, or four additional peaks at 9.9, 11.7, 16.6 and 29.7 deg-2-theta±0.1 deg 2-theta.

Crystalline Form T14 of Ivosidenib may be characterized by each of the above characteristics alone/or by all possible combinations, e.g. by XRPD pattern having peaks at 10.3, 12.4, 17.8, 20.0, 29.2 and 31.7 deg-2-theta±0.2 deg 2-theta; an XRPD pattern as depicted in FIG. 15; and a TGA thermogram spectrum as depicted in FIG. 16.

Crystalline Form T14 of Ivosidenib may be a hydrate, such as a monohydrate, dihydrate, or hydrate fractions there between. In embodiments, crystalline Form T14 is monohydrate. The water content in crystalline Form T14 may be between 2.0% to 5.0%, between 2.2% to 4.5%, between 2.5 to 4.0%, between 2.5 to 3.5%, between 2.5 to 3.0%, as determined by TGA and Karl Fischer titration method. Preferably, the water content in crystalline Form T14 is about 3.0%.

The present disclosure further comprises a crystalline form of Ivosidenib designated as Form T15. The crystalline Form T15 of Ivosidenib can be characterized by data selected from one or more of the following: an XRPD pattern having peaks at 7.4, 18.0, 19.8, 26.1 and 27.2 deg-2-theta±0.2 deg 2-theta; an XRPD pattern as depicted in FIG. 17; and combinations of these data. Crystalline Form T15 of Ivosidenib may alternatively or additionally be characterized by data selected from one or more of the following: a solid state $^{13}$C-NMR spectrum with peaks at peaks at 173.2, 168.4, 134.9, 131.5 and 127.7 ppm±0.2 ppm; or by a solid state $^{13}$C-NMR spectrum having the following chemical shift absolute differences from a peak at 58.1 ppm±2 ppm of 115.1, 110.3, 76.8, 73.4 and 69.6 ppm±0.1 ppm; or by a solid state $^{13}$C NMR spectrum having chemical shift difference from a peak at 173.2 ppm±1 ppm of 115.1 ppm±0.1 ppm; or by a solid state $^{13}$C-NMR spectrum substantially as depicted in FIG. 29; or combinations of these data.

Crystalline Form T15 of Ivosidenib may be further characterized by the XRPD pattern having peaks at 7.4, 18.0, 19.8, 26.1 and 27.2 deg-2-theta±0.2 deg 2-theta, and also having one, two, three, four or five additional peaks selected from 12.4, 12.9, 16.2 and 17.1 deg-2-theta±0.2 deg 2-theta.

Crystalline Form T15 of Ivosidenib may be characterized by each of the above characteristics alone/or by all possible combinations, e.g. by XRPD pattern having peaks at 7.4, 18.0, 19.8, 26.1 and 27.2 deg-2-theta±0.2 deg 2-theta; an XRPD pattern as depicted in FIG. 17; and a TGA thermogram spectrum as depicted in FIG. 18.

Crystalline Form T15 of Ivosidenib may be a hydrate, in embodiments a monohydrate. In embodiments crystalline Form T15 is monohydrate. The water content in crystalline Form T15 may be between 2.0% to 5.0%, between 2.2% to 4.5%, between 2.5 to 4.0%, between 2.5 to 3.5%, between 2.5 to 3.0%, as determined by TGA and Karl Fischer titration method. In embodiments, the water content in crystalline Form T15 is about 3.4%.

The present disclosure further comprises a crystalline form of Ivosidenib designated as Form T16. The crystalline Form T16 of Ivosidenib can be characterized by data selected from one or more of the following: an XRPD pattern having peaks at 3.8, 11.4, 13.1, 18.8 and 21.8 deg-2-theta±0.2 deg 2-theta; an XRPD pattern as depicted in FIG. 19; and combinations of these data. Crystalline Form T16 of Ivosidenib may be further characterized by the XRPD pattern having peaks at 3.8, 11.4, 13.1, 18.8 and 21.8 deg-2-theta±0.2 deg 2-theta, and also having one, two, three, four or five additional peaks selected from 7.8, 19.8, 25.6 and 27.7 deg-2-theta±0.2 deg 2-theta.

Crystalline Form T16 of Ivosidenib may be characterized by each of the above characteristics alone/or by all possible combinations, e.g. by XRPD pattern having peaks at 3.8, 11.4, 13.1, 18.8 and 21.8 deg-2-theta±0.2 deg 2-theta and an XRPD pattern as depicted in FIG. 19. Crystalline Form T16 may be a solvate. Crystalline Form T16 may be an ethanol solvate.

The present disclosure further comprises a crystalline form of Ivosidenib designated as Form T17. The crystalline Form T17 of Ivosidenib can be characterized by data selected from one or more of the following: an XRPD pattern having peaks at 3.7, 7.3, 9.3, 12.2, and 15.8 deg-2-theta±0.2 deg 2-theta; an XRPD pattern as depicted in FIG. 20; and combinations of these data. Crystalline Form T17 of Ivosidenib may be further characterized by the XRPD pattern having peaks at 3.7, 7.3, 9.3, 12.2, and 15.8 deg-2-theta±0.2 deg 2-theta, and also having one, two, three, four or five additional peaks selected from 11.3, 13.5, 18.8 and 22.5 deg-2-theta±0.2 deg 2-theta.

Crystalline Form T17 of Ivosidenib may be characterized by each of the above characteristics alone/or by all possible combinations, e.g. by XRPD pattern having peaks at 3.7, 7.3, 9.3, 12.2, and 15.8 deg-2-theta±0.2 deg 2-theta and an XRPD pattern as depicted in FIG. 20. Crystalline Form T17 may be a solvate. Crystalline Form T17 may be an isopropyl alcohol solvate.

The present disclosure further comprises a crystalline form of Ivosidenib designated as Form T18. The crystalline Form T18 of Ivosidenib can be characterized by data selected from one or more of the following: an XRPD pattern having peaks at 6.2, 9.9, 18.7, 26.3 and 32.0 deg-2-theta±0.2 deg 2-theta; an XRPD pattern as depicted in FIG. 21; and combinations of these data. Crystalline Form T18 of Ivosidenib may be further characterized by the XRPD pattern having peaks at 6.2, 9.9, 18.7, 26.3 and 32.0 deg-2-theta±0.2 deg 2-theta, and also having one, two, three, four or five additional peaks selected from 7.9, 20.0, 21.9 and 25.5 deg-2-theta±0.2 deg 2-theta.

Crystalline Form T18 of Ivosidenib may be characterized by each of the above characteristics alone/or by all possible combinations, e.g. by XRPD pattern having peaks at 6.2, 9.9, 18.7, 26.3 and 32.0 deg-2-theta±0.2 deg 2-theta and an XRPD pattern as depicted in FIG. 21. Crystalline Form T18 may be a solvate. Crystalline Form T18 may be a 2-methoxyethanol solvate.

The present disclosure further comprises a crystalline form of Ivosidenib designated as Form T19. The crystalline Form T19 of Ivosidenib can be characterized by data selected from one or more of the following: an XRPD pattern having peaks at 3.9, 7.9, 11.4, 13.0 and 15.2 deg-2-theta±0.2 deg 2-theta; an XRPD pattern as depicted in FIG. 22; and combinations of these data. Crystalline Form T19 of Ivosidenib may be further characterized by the XRPD pattern having peaks at 21.8, 23.3 and 27.4 deg-2-theta±0.2 deg 2-theta, and also having one, two, three, four or five additional peaks selected from 7.9, 20.0, 21.9 and 25.5 deg-2-theta±0.2 deg 2-theta.

Crystalline Form T19 of Ivosidenib may be characterized by each of the above characteristics alone/or by all possible combinations, e.g. by XRPD pattern having peaks at 3.9, 7.9, 11.4, 13.0 and 15.2 deg-2-theta±0.2 deg 2-theta and an XRPD pattern as depicted in FIG. 22. Crystalline Form T19 may be a solvate. Crystalline Form T19 may be an acetone solvate.

The present disclosure further comprises a crystalline form of Ivosidenib designated as Form T20. The crystalline Form T20 of Ivosidenib can be characterized by data selected from one or more of the following: an XRPD pattern having peaks at 10.9, 12.5, 23.0, 23.7 and 24.3 deg-2-theta±0.2 deg 2-theta; an XRPD pattern as depicted in FIG. 23; and combinations of these data. Crystalline Form T20 of Ivosidenib may be further characterized by the XRPD pattern having peaks at 10.9, 12.5, 23.0, 23.7 and 24.3 deg-2-theta±0.2 deg 2-theta, and also having one, two, three, four or five additional peaks selected from 9.2, 15.9, 16.8 and 21.8 deg-2-theta±0.2 deg 2-theta.

Crystalline Form T20 of Ivosidenib may be characterized by each of the above characteristics alone/or by all possible combinations, e.g. by XRPD pattern having peaks at 10.9, 12.5, 23.0, 23.7 and 24.3 deg-2-theta±0.2 deg 2-theta and an XRPD pattern as depicted in FIG. 23. Crystalline Form T20 may be a solvate. Crystalline Form T20 may be a dichloromethane solvate.

The present disclosure further comprises a crystalline form of Ivosidenib designated as Form T21. The crystalline Form T21 of Ivosidenib can be characterized by data selected from one or more of the following: an XRPD pattern having peaks at 5.7, 6.9, 8.8, 12.8 and 18.4 deg-2-theta±0.2 deg 2-theta; an XRPD pattern as depicted in FIG. 24; and combinations of these data. Crystalline Form T21 of Ivosidenib may be further characterized by the XRPD pattern having peaks at 5.7, 6.9, 8.8, 12.8 and 18.4 deg-2-theta±0.2 deg 2-theta, and also having one, two, three, four or five additional peaks selected from 7.9, 10.0, 14.8 and 15.0 deg-2-theta±0.2 deg 2-theta.

Crystalline Form T21 of Ivosidenib may be characterized by each of the above characteristics alone/or by all possible combinations, e.g. by XRPD pattern having peaks at 5.7, 6.9, 8.8, 12.8 and 18.4 deg-2-theta±0.2 deg 2-theta and an XRPD pattern as depicted in FIG. 24. Crystalline Form T21 may be a solvate. Crystalline Form T21 may be an MTBE solvate.

The present disclosure also provides the solid state forms of Ivosidenib of the present disclosure for use in the preparation of other solid state forms of Ivosidenib, Ivosidenib salts and solid state forms thereof.

The present disclosure further encompasses processes for preparing Ivosidenib salt or solid state forms thereof. The process includes preparing the solid state forms of the present disclosure, and converting it to Ivosidenib salt. The conversion can be done, for example, by processes including reacting the obtained Ivosidenib solid state form with an appropriate acid to obtain the corresponding acid-addition salt.

The present disclosure also provides the solid state forms of Ivosidenib of the present disclosure of use in the preparation of solid dispersions of Ivosidenib or Ivosidenib salts. The solid dispersion of Ivosidenib may include a solid state form of Ivosidenib according to any aspect or embodiment of the invention described herein, and/or may include amorphous Ivosidenib.

The present disclosure also encompasses processes for the preparation of solid dispersions of Ivosidenib from the solid state forms of the present disclosure. The process for the preparation of solid dispersions of Ivosidenib includes preparing the solid state form of Ivosidenib of the present disclosure, and combining it with a pharmaceutically acceptable solid-dispersion carrier or one or more polymer(s) to form a solid dispersion. The process for preparing the solid dispersion of Ivosidenib may include solvent evaporation, coprecipitation, melting, co-grinding, spray-drying, lyophilization or melt extrusion, of Ivosedinib with at least one pharmaceutically acceptable solid-dispersion carrier. In embodiments solid dispersions can be formed by a co-precipitate or a co-melt of the solid state form of Ivosidenib of the present disclosure with at least one pharmaceutically acceptable solid-dispersion carrier. Solid dispersions can be formed by a co-precipitate or a co-melt of the solid state form of Ivosidenib of the present disclosure with one or more polymer(s). Solid dispersions can also be formed by combining a solid state form of Ivosidenib of the present invention with at least one pharmaceutically acceptable solid-dispersion carrier. In embodiments solid dispersions can also be formed by combining a solid state form of Ivosidenib of the present invention with one or more polymer(s) in the presence of a solvent or solvent mixture, followed by mixing and removal of the solvent or solvent mixture. Removal of the solvent or solvent mixture can be done by vacuum drying, spray drying, tray drying, lyophilization, or other drying procedures. The solid dispersion formed in the above process may include amorphous Ivosidenib.

The pharmaceutically acceptable solid-dispersion carrier may be a polymer. The polymer can be selected from: a polyvinyl pyrrolidone, a polyethylene glycol and a polymethacrylate, a cyclodextrin, a cellulosic polymer (particularly wherein the cellulosic polymer is: hydroxypropyl methylcellulose, ethylcellulose, hydroxypropyl cellulose, hydroxypropyl methyl cellulose acetate succinate, hydroxypropyl methylcellulose phthalate, a carboxymethyl cellulose), a methacrylic acid-methyl methacrylate copolymer, an acrylic acid-methacrylate polymer, or a polyol or a polyol polymer); in embodiments wherein the polymer is a cellulosic polymer; in other embodiments wherein the cellulosic polymer is hydroxypropyl methylcellulose, ethylcellulose, hydroxypropyl cellulose, hydroxypropyl methyl cellulose acetate succinate, or hydroxypropyl methylcellulose phthalate.

The present disclosure also encompasses solid dispersions of Ivosidenib including the solid state form of Ivosidenib according to the present disclosure.

In another embodiment, the present disclosure encompasses the above described solid state forms of Ivosidenib for use in the preparation of pharmaceutical compositions and/or formulations, optionally for the treatment of cancer, particularly for the treatment of advanced hematologic malignancies, such as acute myelogenous leukemia (AML), cholangiocarcinoma, glioma, myelodysplastic syndromes, or solid tumors.

In another embodiment, the present disclosure encompasses the use of the above described solid state forms of Ivosidenib for the preparation of pharmaceutical compositions and/or formulations. The present disclosure also provides the solid state forms of Ivosidenib of the present disclosure for use in the preparation of pharmaceutical compositions and/or formulations.

The present disclosure further provides pharmaceutical compositions including the solid state form of Ivosidenib according to the present disclosure.

The present disclosure further encompasses pharmaceutical compositions and/or formulations including solid dispersions prepared by the solid state forms of Ivosidenib of the present disclosure.

The present disclosure further encompasses pharmaceutical compositions and/or formulations including solid dispersions comprising the solid state forms of Ivosidenib of the present disclosure.

In yet another embodiment, the present disclosure encompasses pharmaceutical formulations including the above described solid state form of Ivosidenib and at least one pharmaceutically acceptable excipient.

The present disclosure encompasses processes to prepare said formulations of Ivosidenib including combining one or more of the above solid state forms of Ivosidenib and at least one pharmaceutically acceptable excipient.

The solid state forms of Ivosidenib as defined herein, as well as the pharmaceutical compositions or formulations thereof and at least one pharmaceutical acceptable excipient can be used as medicaments, particularly for the treatment cancer, particularly for the treatment of advanced hematologic malignancies, such as acute myelogenous leukemia (AML), cholangiocarcinoma, glioma, myelodysplastic syndromes, or solid tumors.

The present disclosure also provides methods of treating cancer, particularly for the treatment of advanced hematologic malignancies, such as acute myelogenous leukemia (AML), cholangiocarcinoma, glioma, myelodysplastic syndromes, or solid tumors, including administering a therapeutically effective amount of one or more of the solid state forms of Ivosidenib disclosed in the present disclosure, or at least one of the above pharmaceutical compositions or formulations, to a subject suffering from cancer, particularly for the treatment of advanced hematologic malignancies, such as acute myelogenous leukemia (AML), cholangiocarcinoma, glioma, myelodysplastic syndromes, or solid tumors, or otherwise in need of the treatment.

The present disclosure also provides use of the solid state form of Ivosidenib of the present disclosure, or at least one of the above pharmaceutical compositions or formulations for the manufacture of a medicament for treating cancer, particularly for the treatment of advanced hematologic malignancies, such as acute myelogenous leukemia (AML), cholangiocarcinoma, glioma, myelodysplastic syndromes, or solid tumors.

The present disclosure further provides an improved process for the preparation of Ivosidenib. The disclosed process for the preparation of Ivosidenib is suitable for industrial scale, avoids hazardous and unstable intermediates, has high yields and leads to a chemical and enantiomeric pure product.

The present disclosure provides a process for the preparation of Ivosidenib according to reaction scheme 1:

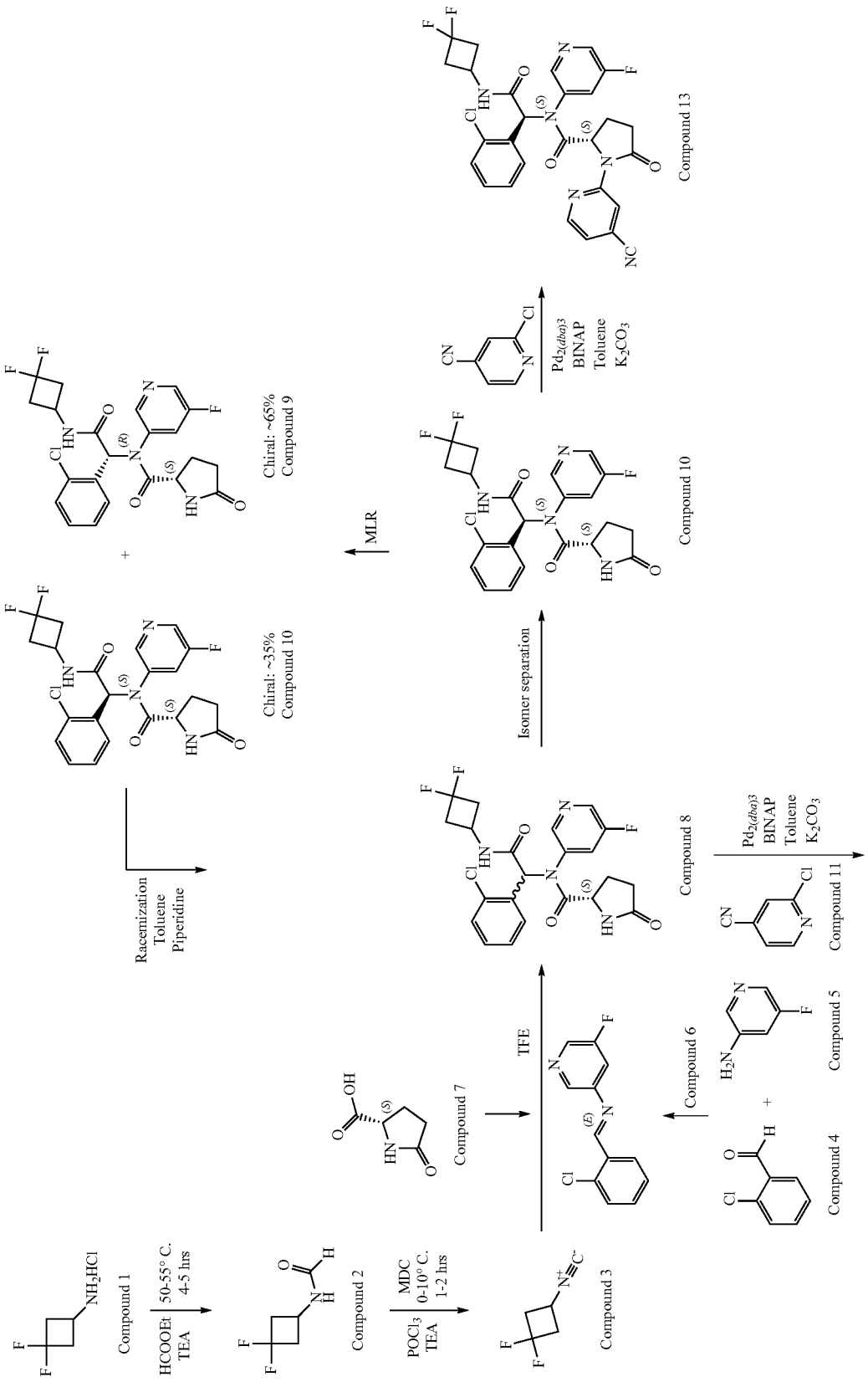

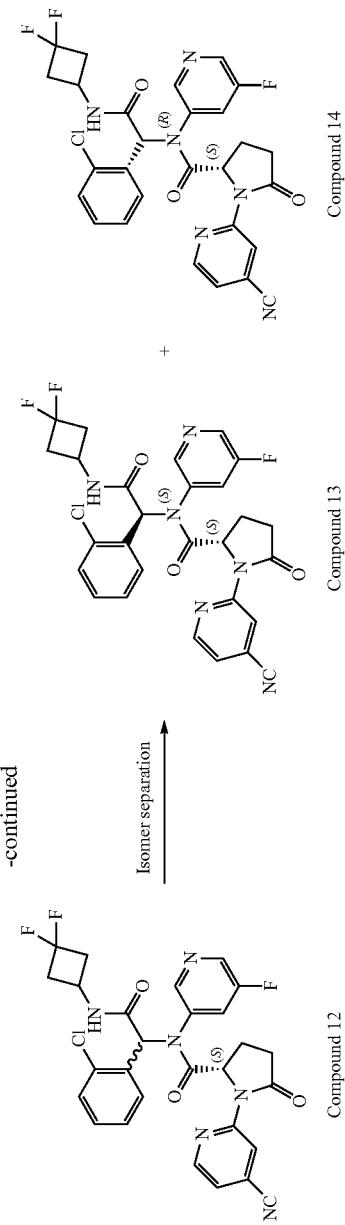

The present disclosure further provides compounds (8), (10) and (9) according to the following structures:

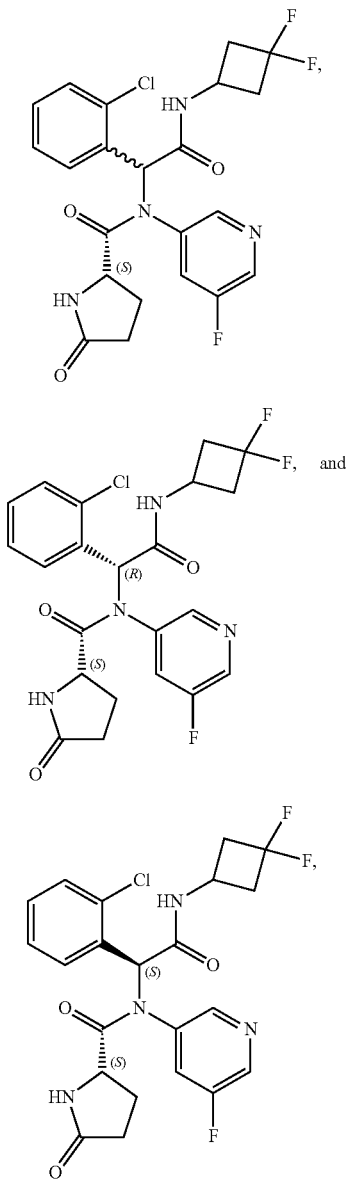

Compound 8 ((S)—N-(1-(2-chlorophenyl)-2-((3,3-difluorocyclobutyl)amino)-2-oxoethyl)-N-(5-fluoropyridin-3-yl)-5-oxopyrrolidine-2-carboxamide) is the racemic mixture of compound (10) ((S)—N—((S)-1-(2-chlorophenyl)-2-((3,3-difluorocyclobutyl)amino)-2-oxoethyl)-N-(5-fluoropyridin-3-yl)-5-oxopyrrolidine-2-carboxamide) and compound (9) (((S)—N—((R)-1-(2-chlorophenyl)-2-((3,3-difluorocyclobutyl)amino)-2-oxoethyl)-N-(5-fluoropyridin-3-yl)-5-oxopyrrolidine-2-carboxamide). Compound (10) preferably contains 0.05 to 3.0%, preferably 0.07 to 2.0%, more preferably 0.1 to 1.0%, most preferably less than 0.5% of compound (9).

The present disclosure provides a process for the preparation of compound (10) comprising selective crystallization of compound (8) in the presence of a base. The base can be selected from an amine, or an alkali metal carbonate or alkali metal hydrogencarbonate. In embodiments the base is selected from piperidine, pyrrolidine, 1,8-Diazabicyclo[5.4.0]undec-7-ene (DBU), cesium carbonate; and in some embodiments wherein the base is piperidine. The crystallization can be carried out in a solvent selected from toluene, trifluoroethanol (TFE), acetonitrile, N,N-dimethylformamide (DMF), toluene:water mixture, preferably the solvent is toluene. Compound 10 can then be further converted to Ivosidenib (compound 13).

The present disclosure further provides a process for Ivosidenib (compound 13) including a Pd-catalyzed amination of compound 10 (in embodiments wherein compound 10 is prepared by the process according to the invention as described above) in the presence of a ligand selected from the group consisting of: (S)-(−)-(1,1'-binaphthalene-2,2'-diyl)bis(diphenylphosphine) [S(−) BINAP], 2-dicyclohexylphosphino-2',6'-dimethoxybiphenyl [S-Phos], (R) or (S)-(+)-5,5'-bis(diphenylphosphino)-4,4'-bi-1,3-benzodioxole [SEGPHOS] and (4-(N,N-dimethylamino)phenyl)di-tert-butyl phosphine [A-Phos], preferably wherein the ligand is R(+) BINAP. The reaction can be carried out in a solvent comprising an ester (preferably a $C_3$-$C_8$ ester), or a $C_{4-10}$ hydrocarbon (preferably a $C_{6-10}$ aromatic hydrocarbon), or a mixture thereof, and preferably wherein the solvent is selected from methylacetate, ethylacetate, isopropylacetate, propylacetate, toluene, or a mixture thereof, preferably wherein the solvent is ethylacetate.

A mixture of compound 10 and compound 9, which may be obtained as the by-product of the selective crystallization of compound 8, remain in solution, which contains an excess of compound 9. From this solution, compound 10 can be enriched by removal of the solvent and recrystallization of the residue from another solvent in the presence of a base. The residue contains an excess of compound 9, preferably more than 55%, more preferably more than 65% of compound 9. The base can be selected from an amine, or an alkali metal carbonate or alkali metal hydrogencarbonate. Preferably the base is selected from piperidine, pyrrolidine, 1,8-Diazabicyclo[5.4.0]undec-7-ene (DBU), cesium carbonate; and preferably wherein the base is piperidine. The crystallization can be carried out in a solvent selected from toluene, trifluoroethanol (TFE), acetonitrile, N,N-dimethylformamide (DMF), toluene:water mixture, preferably the solvent is toluene. The obtained solid from the crystallization contains an excess of compound 10 versus compound 9, preferably the residue contains more than 55%, preferably more than 65% of compound 10.

The present disclosure further provides a process for compound (8) including reaction of compound 3 (1, 1-difluoro-3-isocyanocyclobutane), compound 6 (1-(2-chlorophenyl)-N-(5-fluoropyridin-3-yl) methanimine) and compound 7 ((S)-5-oxopyrrolidine-2-carboxylic acid). The compound 6 is reacted in isolated form (i.e. compound (6) is not prepared in situ in the reaction mixture. The reaction to prepare compound (8) may be carried out in a solvent selected from selected from $C_1$-$C_5$ alcoholic solvents, preferably methanol or ethanol, $C_1$-$C_5$ halogenated alcoholic solvents, preferably 2-chloroethanol, more preferably 2,2,2-trifluoroethanol (TFE). In embodiments the reaction is carried out at a pH of 6.5 to 8.5, more preferably of 7.0 to 8.0. The compound 6 employed in this process is preferably prepared according to the process as described below. The compound 3 employed in this process is preferably prepared according to the process as described below.

The present disclosure further provides a process for compound 6 including reaction of compound 4 (2-chlorobenzaldehyde) and compound 5 (5-fluoropyridin-3- amine) and isolation of compound 6, in embodiments wherein the isolation of compound 6 includes azeotropic removal of water. The reaction to prepare compound (6) is preferably carried out in a solvent selected from n-heptane, toluene, xylene, cyclohexane, dichloromethane, $C_1$-$C_5$ alcohols or halogenated $C_1$-$C_5$ alcohols.

The present disclosure further provides a process for preparing compound 3 (1, 1-difluoro-3-isocyanocyclobutane) including reaction of compound 2 (N-(3, 3-difluorocyclobutyl) formamide) with $SOCl_2$, 1,3-bis(dicyclohexylphosphino) propane [DCPP], or $POCl_3$, and preferably $POCl_3$, in the presence of a base (preferably wherein the base is triethylamine (TEA). At the end of the reaction a base is added, in embodiments an inorganic base, more preferably wherein the base is selected from an alkali metal carbonate, an alkali metal hydrogen carbonate, or alkali metal hydroxide, or ammonia, is added to the reaction mixture, more preferably wherein the base is selected from the group consisting of: $NaHCO_3$, $Na_2CO_3$, NaOH, $K_2CO_3$, and ammonia, most preferably wherein the inorganic base is ammonia. Compound 3 can be used without isolation in the further reaction with compound 6 and compound 7 to obtain compound 8.

Having described the disclosure with reference to certain preferred embodiments, other embodiments will become apparent to one skilled in the art from consideration of the specification.

The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods
X-Ray Powder Diffraction Method:
X-ray diffraction was performed on X-Ray powder diffractometer: Bruker D8 Advance; CuK_radiation (λ=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.
Measurement Parameters:
Scan range: 2-40 degrees 2-theta;
Scan mode: continuous;
Step size: 0.05 degrees;
Time per step: 0.5 s;
Sample spin: 30 rpm;
Sample holder: PMMA specimen holder
All X-Ray Powder Diffraction peak values are calibrated with regard to standard silicon spiking in the sample. Procedure for Thermo Gravimetric Analysis (TGA) for Form T11
Thermogravimetric analysis was conducted on TA instrument TGA Q-500 thermogravimetric analyzer. About 4-5 mg sample was placed into a tared TGA crucible and placed into a TGA furnace. The furnace was heated under nitrogen at a heating rate of 10° C./min up to 300° C.
Procedure for Thermo Gravimetric Analysis (TGA) for Forms T14 and T15:
Thermogravimetric analysis was conducted on a TA instrument Q500 thermogravimetric analyzer. About 9.4 mg sample was placed into a tared TGA crucible and placed into a TGA furnace. The furnace was heated under nitrogen at a heating rate of 10° C./min up to 250° C.

Procedure for Differential Scanning Calorimetry (DSC)
DSC was performed using TA DSC Q-2000 differential scanning calorimetry. About 2 mg sample was accurately weighed into an aluminium pan and covered with a lid having hole and the crimped. The cell was equilibrated at 20° C. and heated at rate of 10° C./min up to 350° C. under nitrogen atmosphere.
Karl Fischer Method:
Water content analysis was performed on Metrohm 890 Titando instrument. About 100 mg sample was added to the titrator, the water content is measured in % w/w by measuring the amount of iodine consumed as a result of reaction with water in the sample.
Solid-State $^{13}$CNMR Method
Solid-state $^{13}$C NMR spectra were recorded with variable amplitude cross polarization, magic angle spinning and high power proton decoupling using a BRUKER Avance III+ spectrometer operating at 400 MHZ at room temperature. A probe using 4 mm o.d. zirconia rotors was employed. The operation conditions were: contact time: 3 ms; recycle delay: 2s; 5100 scans and spin rate of 11 KHz. Chemical shifts were referenced via a replacement sample of glycine (carboxyl carbon chemical shift assigned as 176.03 ppm relative to the signal of tetramethyl silane).

EXAMPLES

Ivosidenib starting material can be prepared by those skilled in the art as already disclosed, e.g. in U.S. Pat. No. 9,474,779.

Example 1 Preparation of Amorphous Ivosidenib

Ivosidenib 2.0 g was dissolved in tert-butymethylether (80 mL) at 22-25° C. and obtained a clear solution. The reaction mixture was subjected to rotary-evaporator distillation under reduced pressure at 40-45° C. Solid material was obtained and isolated at 22-25° C. The obtained solid was amorphous form of Ivosidenib analyzed by XRD. (Yield: 1.95 g).

Example 2: Preparation of Ivosidenib Form T1

Ivosidenib 0.050 g was dissolved in anisole (0.2 mL) at 22-25° C. and obtained a clear solution. The reaction mixture was kept for slow solvent evaporation in a 15 mL round bottom test tube and covered with paraffin film with a hole at 20-25° C. Solid material was obtained at 25-30° C. after four days. The obtained solid was isolated/filtered under vacuum and kept under suction for about 10-20 minutes at 25-30° C. to obtain Ivosidenib anisole solvate designated as Form T1.

Example 3: Preparation of Ivosidenib Form T2

Ivosidenib 0.050 g was dissolved in isoamyl alcohol (0.2 mL) at 22-25° C. and obtained a clear solution. The reaction mixture was kept for slow solvent evaporation in a 15 mL round bottom test tube and covered with paraffin film with a hole at 20-25° C. Solid material was obtained at 25-30° C. after four days. The obtained solid was isolated/filtered under vacuum and kept under suction for about 10-20 minutes at 25-30° C. to obtain Ivosidenib isoamyl alcohol solvate designated as Form T2.

Example 4: Preparation of Ivosidenib Form T3

Ivosidenib 0.050 g was dissolved in propyl acetate (0.1 mL) at 22-25° C. and obtained a clear solution. The reaction mixture was kept for slow solvent evaporation in a 15 mL round bottom test tube and covered with paraffin film with a hole at 20-25° C. Solid material was obtained at 25-30° C. after 3-4 days. The obtained solid was isolated at 25-30° C. to obtain Ivosidenib propylacetate solvate designated as Form T3.

Example 5: Preparation of Ivosidenib Form T4

Ivosidenib 0.20 g was dissolved in methyl acetate (1.2 mL) at 22-25° C. and obtained a clear solution. The reaction mixture was kept in a 10 mL round bottom test tube with magnetic stirring for 24 hours and solid material was obtained at 25-30° C. after 24 hours. The obtained solid was isolated at 25-30° C. to obtain Ivosidenib methyl acetate solvate designated as Form T4.

Example 6: Preparation of Ivosidenib Form T5

Ivosidenib 0.20 g was dissolved in ethyl acetate (1.2 mL) at 22-25° C. and obtained a clear solution. The reaction mixture was kept 10 mL round bottom test tube with magnetic stirring for 24 hours and solid material was obtained at 25-30° C. after 24 hours. The obtained solid was isolated at 25-30° C. to obtain Ivosidenib ethyl acetate solvate designated as Form T5.

Example 7: Preparation of Ivosidenib Form T6

Ivosidenib 0.050 g was dissolved in dimethyl sulfoxide (0.2 mL) at 22-25° C. and obtained a clear solution. The reaction mixture was kept for slow solvent evaporation in a 15 mL round bottom test tube and covered with paraffin film with a hole at 20-25° C. Solid material was obtained at 25-30° C. after 3-4 days. The obtained solid was isolated at 25-30° C. to obtain Ivosidenib DMSO solvate designated as Form T6.

Example 8: Preparation of Ivosidenib Form T7

Ivosidenib 0.050 g was dissolved in 1,3-dioxolane (0.1 mL) at 22-25° C. and obtained a clear solution. The reaction mixture was kept for slow solvent evaporation in a 15 mL round bottom test tube and covered with paraffin film with a hole at 20-25° C. Solid material was obtained at 25-30° C. after four days. The obtained solid was isolated at 25-30° C. to obtain Ivosidenib 1,3-dioxolane solvate designated as Form T7.

Example 9: Preparation of Ivosidenib Form T8

Ivosidenib 0.050 g was dissolved in p-Xylene (0.2 mL) at 22-25° C. and obtained a clear solution. The reaction mixture was kept for slow solvent evaporation in a 15 mL round bottom test tube and covered with paraffin film with a hole at 20-25° C. Solid material was obtained at 25-30° C. after four days. The obtained solid was isolated at 25-30° C. to obtain Ivosidenib p-xylene solvate designated as Form T8.

Example 10: Preparation of Ivosidenib Form T9

Ivosidenib 0.050 g was dissolved in 1,2-dimethoxyethane (0.2 mL) at 22-25° C. and obtained a clear solution. The reaction mixture was kept for slow solvent evaporation in a 15 mL round bottom test tube and covered with paraffin film with a hole at 20-25° C. Solid material was obtained at 25-30° C. after four days. The obtained solid was isolated at 25-30° C. to obtain Ivosidenib 1,2-dimethoxyethane solvate designated as Form T9.

Example 11: Preparation of Ivosidenib Form T10

Ivosidenib 0.050 g was dissolved in chlorobenzene (0.2 mL) at 22-25° C. and obtained a clear solution. The reaction mixture was kept for slow solvent evaporation in a 15 mL round bottom test tube and covered with paraffin film with a hole at 20-25° C. Solid material was obtained at 25-30° C. after four days. The obtained solid was isolated at 25-30° C. to obtain Ivosidenib chlorobenzene solvate designated as Form T10.

Example 12: Preparation of Ivosidenib Form T11

Ivosidenib (Form T2, 0.050 g) was charged in a 2.5 mL glass vial and 1.0 mL n-heptane was added. The vial was closed by PTFE septa with a screw cap and the slurry was kept for magnetic stirring for 2-days at 20-25° C. The slurry was filtered and washed with 1.0 mL n-heptane and suck dried for 10-15 minutes at 20-25° C. The obtained solid was analyzed by XRPD and designated as Form T11 of Ivosidenib.

Example 13: Preparation of Ivosidenib Form T12

Ivosidenib (0.050 g) was charged into a 15 mL round bottom test tube and 0.8 mL isopropyl-acetate was added at 20-25° C. The clear solution was covered by paraffin film with a hole and kept for slow solvent evaporation at 20-25° C. without agitation. Solid material was obtained after 7-days. The obtained solid was analyzed by XRPD and designated as Form T12.

Example 14: Preparation of Ivosidenib Form T13

Ivosidenib (0.050 g) was charged into a 15 mL round bottom test tube and 1.0 mL isobutyl-acetate was added at 20-25° C. The obtained clear solution was covered by paraffin film with a hole and kept for slow solvent evaporation at 20-25° C. without agitation. Solid material was obtained at 20-25° C. after 7-days. The obtained solid was analyzed by PXRD and designated as Form T13.

Example 15: Preparation of Ivosidenib Form T14

Ivosidenib (amorphous, 0.100 g) was taken into a 2 mL glass vial and 0.2 mL methanol was added at 20-25° C. to obtained a clear solution. The reaction mixture was kept under magnetic stirring for 24 hours at 20-25° C. The reaction mixture was filtered under vacuum and suck dried for 5-10 minutes at 20-25° C. The obtained solid was analyzed by PXRD and designated as Form T14.

Form T14 is a hydrate showing moisture content of 2.7% (KF Titration method) and the weight loss represent a loss of about 2.786% of the weight of the sample as the temperature is changed from 27.1° C. to 170° C. (TGA data).

Example 16: Preparation of Ivosidenib Form T15

Ivosidenib (1.0 g) was taken in a 50 mL reaction flask and added 4.0 mL methanol under stirring at 200 rpm and obtained a clear solution at 20-25° C. The clear solution was kept under stirring for 6 hours at 25° C. in a closed vial. The reaction mixture was vacuum-filtered and dried for 10-20 minutes at 20-25° C. to obtain Ivosidenib Form T15 (Yield: 0.85 g).

Form T15 has a water content of 3.39% according to KF Titration method. Form T15 was also analyzed by TGA and the weight loss represents a loss of about 3.899% of the weight of the sample as the temperature is changed from 27.1° C. to 170° C.

Example 17: Preparation of Ivosidenib Form T16

Ivosidenib (0.25 g) was taken in a 20 mL reaction tube and added 1.0 mL ethanol under magnetic stirring at 200 rpm at 20-25° C. The clear solution was kept under magnetic stirring at 25° C. in a closed reaction tube. After 24 hours, the slurry mass was vacuum-filtered for 10-15 minutes at 20-25° C. to obtain Ivosidenib Form T16.

Example 18: Preparation of Ivosidenib Form T17

Ivosidenib (0.25 g) was taken in a 20 mL reaction tube and added 1.0 mL isopropyl alcohol under magnetic stirring at 200 rpm at 20-25° C. The clear solution was kept under magnetic stirring at 25° C. in a closed reaction tube. After 24 hours, the slurry mass was vacuum-filtered for 10-15 minutes at 20-25° C. to obtain Ivosidenib Form T17.

Example 19: Preparation of Ivosidenib Form T18

Ivosidenib (0.050 g) was dissolved in 2-methoxyethanol (0.2 mL) in a 15 mL round bottom test tube at 22-25° C. The clear solution was covered with a paraffin film with a hole and kept for slow solvent evaporation at 20-25° C. After 7 days, the obtained solid material was analyzed by XRPD and designated as Ivosidenib Form T18.

Example 20: Preparation of Ivosidenib Form T19

Ivosidenib (Amorphous, 0.100 g) was taken in a 6 mL glass vial and dissolved in 0.2 mL acetone under magnetic stirring at 35-40° C. A clear solution was obtained, immediately cooled to 0° C. and maintained for about 4 hours under stirring. No precipitation was observed.

The solution was then kept without agitation at 2-8° C. in a refrigerator. After 2-days obtained solid was analyzed by PXRD and designated as Form T19.

Example 21: Preparation of Ivosidenib Form T20

Ivosidenib (amorphous, 0.100 g) was taken in a 6 mL glass vial and dissolved in 0.2 mL dichloromethane under magnetic stirring at 35-40° C. A clear solution was obtained, immediately cooled to 0° C. and maintained for 4-5 hours under stirring. The solution was then kept without agitation at 2-8° C. in a refrigerator. After 2-days the obtained solid material was analyzed by PXRD and designated as Form T20.

Example 22: Preparation of Ivosidenib Form T21

Ivosidenib (Amorphous, 0.100 g) was taken in a 6 mL glass vial and dissolved in 0.2 mL methyl-tert-butylether (MTBE) under magnetic stirring at 60° C. A clear solution was obtained, immediately cooled to 0° C. and maintained for about 4-5 hours under stirring. No precipitation was observed. The solution was then kept without agitation at 2-8° C. in a refrigerator. After 5-days the obtained solid material was analyzed by PXRD and designated as Form T21.

Example 23: Preparation of Amorphous Ivosidenib

Ivosidenib (Form T11) 3.0 g was dissolved in tert-butymethylether (220 mL) at 22-25° C. and obtained a clear solution. The reaction mixture was subjected to rota-vapor distillation under reduced pressure at 40-45° C. Solid material was obtained and isolated at 22-25° C. The obtained solid was amorphous form of Ivosidenib (Yield: 2.8 g).

Definitions of compounds 1-14 in examples 24-47 below are according to Reaction Scheme 1.

Example-24: Preparation of N-(3, 3-difluorocyclobutyl) formamide (Compound 2)

Compound 1 (100 gm, 0.6965 moles) was suspended in ethylformate 152 mL followed by addition of triethylamine (105.72 gm, 1.0447 moles) the reaction mixture was refluxed for the 3-4 hrs, reaction mass was cooled at 20-30° C. followed by addition of water at 20-30° C., organic layer was separated out, aqueous layer again extracted with ethylacetae, both organic layer are combined and distilled out solvents completely under reduced pressure at 40-45° C., to obtained compound 2 as white solid, 86.58 gm (92.0%), HPLC Purity: 97.0-99.0%.

Example-25: Preparation of N-(3, 3-difluorocyclobutvl) formamide (Compound 2)

The solution of compound 1 (5.0 g, 0.0348 moles) and 7.5 mL of formic acid was slowly added trimethylamine (5.30 g, 0.0521 moles), obtained solution was stirred at 60-65° C. for 1-2 hrs, the reaction progress was monitored by GC, then mass was cooled to 20-25° C., product was partitioned with Ethyl acetate and water mixture, distilled off solvent completely under reduced pressure to produce compound 2 as a white solid, 3.10 g (65.95%), HPLC Purity: 98.45%.

Example-26: Preparation of 1, 1-difluoro-3-isocyanocyclobutane (Compound 3)

Compound 2 (10 gm, 0.07401 moles) was suspended in 150 ml of MDC 40 ml Triethyamine (29.4 gm, 0.2865 moles) then the mass was cooled to 5-10° C. followed by addition of POCl$_3$ (13.0 gm, 0.08478 moles) at 5-10° C. the reaction mass was stirred at 5-10° C. for 1.0-2.0 hrs, after reaction completion added slowly 2% ammonia solution 100 ml at 5-10° C., organic layer was separated out and washed with ammonia solution at 5-10° C., organic layer was dried with sodium sulphate, then distilled off the solvent under reduced pressure at 5-10° C. to obtained compound 3, GC Purity: 96.0-98.0%.

Example 27: Preparation of 1, 1-difluoro-3-isocyanocyclobutane (Compound 3)

Compound 2 (1.0 gm, 0.0074 moles) was suspended in 15 ml of MDC 4 ml Triethyamine (2.24 gm, 0.0221 moles) then the mass was cooled to 5-10° C. followed by addition of SOCl$_2$ (0.92 gm, 0.0077 moles) at 5-10° C. the reaction mass was stirred at 5-10° C. for 1.0-2.0 hrs, after reaction completion added slowly 2% ammonia solution 100 ml at 5-10° C., organic layer was separated out and washed with ammonia solution at 5-10° C., organic layer was dried with sodium sulphate, then distilled off the solvent under reduced pressure at 5-10° C. to obtained compound 3 as liquid.

Example 28: Preparation of 1, 1-difluoro-3-isocyanocyclobutane (Compound 3)

Compound 2 (100 gm, 0.7401 moles) was suspended in 600 ml of MDC 400 ml Triethyamine (290.4 gm, 2.8698 moles) then the mass was cooled to 5-10° C. followed by addition of Phenyldichlorophosphate (DCPP) (187.38 gm, 0.8906 moles) (130.0 gm, 0.8478 moles) at 5-10° C. the reaction mass was stirred at 5-10° C. for 1-1.5 hrs, after reaction completion added slowly 5% ammonia solution 500 ml at 5-10° C., organic layer was separated out and washed with ammonia solution at 5-10° C., organic layer was dried with sodium sulphate, then distilled off the solvent under reduced pressure at 5-10° C. to obtained compound 3, HPLC Purity: 96.0-98.0%.

Example-29: Preparation of 1-(2-chlorophenyl)-N-(5-fluoropyridin-3-yl) methanimine (Compound 6)

To a suspension of compound-5 ((5-fluoropyridin-3-amine) (25 g, 0.2229 moles)) in heptane (150 mL) was added slowly compound-4 ((2-chlorobenzaldehyde) (34.48 g, 0.245 mole)) at 20-25° C. the reaction mixture was stirred for 4-6 hrs at reflux temperature and removed azeotropically formed water. The reaction mixture was cooled to 10-15° C. and further stirred for 1h. The product was filtered off and washed with cold heptane (50 mL). The solid was dried under vacuum at 25° C. to afford a white solid (50 g, 95.6% yield); 99.86% HPLC purity. $H^1$NMR, (400 MHz, CDCl3)-7.32 (m, 1H), 7.38 (m, 1H), 7.46 (m, 2H), 8.25 (d, 1H), 8.04 (dd, 2H), 8.93 (s, 1H).

Example-30: Preparation of (S)—N-(1-(2-chlorophenyl)-2-((3,3-difluorocyclobutyl)amino)-2-oxoethyl)-N-(5-fluoropyridin-3-yl)-5-oxopyrrolidine-2-carboxamide (Compound 8)

To a suspension of compound 2 ((N-(3,3-difluorocyclobutyl)formamide) (5 g, 0.037 mole)) in MDC (75 mL) at 25-35° C. added triethyl amine (20 mL, 0.143 mole). The resulting solution was cooled to 0 to −5° C. and added $POCl_3$(4 ml, 0.042 mole). Reaction mass stirred until completion (Monitored by GC). After completion of reaction it was quenched by 2% ammonia solution (15 ml). Layer separated. Organic layer was distilled off and into it 2, 2, 2 trifluoroethanol (80 ml) added. It was cooled to 0-10° C. and into it added compound 6 ((1-(2-chlorophenyl)-N-(5-fluoropyridin-3-yl) methanimine)) (7.81 g, 0.033 mole) and compound 7 (((S)-5-oxopyrrolidine-2-carboxylic acid) (5.01 g, 0.038 mole)) at 0-10° C. and stirred for 1.0-2.0h (monitored by HPLC). After completion of reaction water (35 ml) added and 2,2,2 trifluoroethanol was distilled off under vacuum at 50° C. It was extracted by ethyl acetate (50 ml). Organic layer was washed with saturated bicarbonate solution (35 ml). Organic layer distilled off under vacuum at 50° C. Into crude material 45 ml acetonitrile was added and heated to 70° C. It was gradually cooled to 0-5° C., solid precipitated. It was filtered off, washed with cooled acetonitrile (10 ml) and suck dried. Wet cake further dried under vacuum at 50° C. (8.00 g, 45%) (HPLC purity=100%).

Example 31: Preparation of (S)—N-(1-(2-chlorophenyl)-2-((3,3-difluorocyclobutyl)amino)-2-oxoethyl)-N-(5-fluoropyridin-3-yl)-5-oxopyrrolidine-2-carboxamide (Compound 8) and chiral separation to obtain Compound 10

To a solution of compound 2 ((N-(3,3-difluorocyclobutyl) formamide) (1.25 g, 0.009 mole)) in MDC (30 mL) at 25-35° C. added triethyl amine (5 mL, 0.0359 mole). The resulting solution was cooled to 0 to −5° C. and added $POCl_3$ (1 ml, 0.0106 mole). Reaction mass stirred until completion (Monitored by GC). After completion of reaction it was quenched by 5% aqueous bicarbonate solution (20 ml). Organic layer was distilled off and 2, 2, 2 trifluoroethanol (20 ml) added. It was cooled to 0-10° C. and added compound 6 ((1-(2-chlorophenyl)-N-(5-fluoropyridin-3-yl) methanimine) (1.95 g, 0.0083 mole)) and compound 7 (((S)-5-oxopyrrolidine-2-carboxylic acid) (1.25 g, 0.0097 mole)) at 0-10° C. and stirred for 1.0-2.0h (monitored by HPLC). After completion of reaction water (20 ml) added and 2, 2, 2 trifluoroethanol was distilled off under vacuum at 50° C. It was extracted by MTBE (20 ml). MTBE was distilled off to 10 volumes and stirred 8 hrs at 20-25° C. Solid precipitated, it was filtered off, washed by 5 ml MTBE and suck dried. Wet cake further dried under vacuum at 50° C. (0.8 g, 18%), (Purity=98.75%, Chiral purity=95.97%).

Example 32: Preparation of (S)—N-(1-(2-chlorophenyl)-2-((3,3-difluorocyclobutyl)amino)-2-oxoethyl)-N-(5-fluoropyridin-3-yl)-5-oxopyrrolidine-2-carboxamide (Compound 8) and its chiral separation to obtain Compound 10

Compound 1 (100 gm, 0.6965 moles) was suspended in ethylformate 152 mL followed by addition of triethylamine (105.72 g, 1.0447 moles) the reaction mixture was refluxed for the 3-4 hrs, added 150 mL toluene and distilled off solvent under vacuum at 50-55° C. till residue volume reached up to 200-250 mL, cool reaction mass to 20-25° C., Charged MDC (700 mL) at 25-35° C. added triethyl amine (282 g, 2.7868 moles). The resulting solution was cooled to 0 to 5° C. and added $POCl_3$ (139.0 gm, 0.9065 mole). Reaction mass was stirred until completion (Monitored by GC) at 5-10° C. After completion of reaction it was quenched by aqueous ammonia solution (200 mL 30% aqueous ammonia solution and 1100 mL water. Organic layer was distilled off and charged 2, 2, 2 trifluoroethanol (600 mL) and it was cooled to 0-10° C. and added compound 6 ((1-(2-chlorophenyl)-N-(5-fluoropyridin-3-yl)methanimine) (131 g, 0.5582 mole)) and compound 7 (((S)-5-oxopyrrolidine-2-carboxylic acid) (81.0 g, 0.6273 mole)) at 0-10° C. and stirred for 1h (monitored by HPLC) at 0-10° C. and raised temperature to 20-25° C. then stirred for 4-5 hrs. After completion of reaction trifluoroethanol was distilled off under vacuum at 50-55° C. till residue volume reached up to 300-350 mL, charged 50 mL trifluoroethannol at 40-45° C. followed by addition of 1000 mL MTBE at 40-45° C., organic layer was washed with 5% sodium carbonate solution at 40-50° C., then cooled to 20-25° C. compound 8 was seeded then charged 750 mL n-heptane then mass was stirred 2-4 hrs at 20-25° C. Precipitated solid was filtered off, to obtained compound 8 (180 g, 53.73%), (Purity=98.75%).

Isolated compound 8 was suspended in 125 mL methylacetate then heated to 50-60° C., added 300 mL of MTBE 50-60° C. stirred 30 min at 50-55° C. then cooled to 40-45° C. seeded Compound 10, then cooled to 20-25° C., then stirred for 1-2 hrs obtained solid was filtered off and dried under vacuum at 45-55° C. to obtained compound 10 (42 g, 12.54%, HPLC Purity: 99.50% and Chiral Purity: >99.80%).

Example 33: Chiral separation of compound 8 to obtain (S)—N—((S)-1-(2-chlorophenyl)-2-((3,3-difluorocyclobutyl)amino)-2-oxoethyl)-N-(5-fluoropyridin-3-yl)-5-oxopyrrolidine-2-carboxamide (Compound 10)

A racemic mixture of compound 8 (5 g, 0.0104 mole) was stirred in ethyl acetate (10 ml) and heated to 65° C. The resulting mixture was stirred at 65° C. for 30 min., the obtained solid was filtered and washed with ethyl acetate (5 mL). The mass was dried under vacuum to afford white solid. (Wt. 250 mg, HPLC purity 99.06%, undesired isomer 0.45%).

Example 34: Chiral separation of compound 8 to obtain (S)—N—((S)-1-(2-chlorophenyl)-2-((3,3-difluorocyclobutyl)amino)-2-oxoethyl)-N-(5-fluoro-pyridin-3-yl)-5-oxopyrrolidine-2-carboxamide (Compound 10)

A racemic mixture of compound 8 (20 g, 0.0416 mole) was added in methyl acetate (20 mL) and the resulting mass was heated to 65° C. to get a clear solution. MTBE (70 mL) was added, stirred the mass and cooled to 20-25° C. The solid thus obtained was filtered and washed with MTBE (40 mL). The mass was dried under vacuum to afford white solid. (wt. 5.1 g, Chiral purity 99.93%, undesired isomer 0.07%).

Example 35: Chiral separation of compound 8 to obtain (S)—N—((S)-1-(2-chlorophenyl)-2-((3, 3-difluorocyclobutyl)amino)-2-oxoethyl)-N-(5-fluoro-pyridin-3-yl)-5-oxopyrrolidine-2-carboxamide (Compound 10)

A racemic mixture of IVS-5 (4 g, 0.0083 moles) was taken in a round bottomed flask and methyl acetate (4 mL) and ethanol 0.12 g (3% w/w) was added. The mass was heated to 58° C. to get a clear solution, cooled to 55° C. MTBE (10 mL) was added followed by cooling to 30° C. Added MTBE (4 mL), stirred the mass and cooled to 20-25° C. The solid thus obtained was filtered and washed with MTBE (12 mL). The mass was dried under vacuum to afford white solid. (wt. 0.9 g, undesired isomer 0.11%).

Example 36: Preparation of (S)—N-(1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (compound 12)

Toluene was degassed by argon bubbling for at least 30 min at 20-30° C., added tris (dibenzylideneacetone)-dipalladium (0) 0.095 gm, 0.000103 moles) and R—(+)—BINAP (0.13 gm, 0.000209 moles) was stirred at 20-30° C. for 1 hrs, compound 8 (10.00 gm, 0.02079 moles), compound 11 (3.17 gm, 0.02287 moles) followed by potassium carbonate (3.45 gm, 0.02496 moles), the reaction mass was heated to reflux until the reaction completion, then the mixture is cooled to 50-60° C., toluene layer was successively washed with 50 ml water followed by addition of 0.80 gm N-acetyl-L-cysteine and the mixture was stirred 1 hrs at 50-60° C. followed by toluene layer was successively washed with 50 ml water twice, toluene layer was distilled off under reduced pressure to obtained crude compound 12 10.00 gm, yield: 83.0%, HPLC Purity: 93.0-96.0%).

Example-37: Preparation of (S)—N—((R)-1-(2-chlorophenyl)-2-((3,3-difluoro cyclobutyl)amino)-2-oxoethyl)-1-(4-cyanopyridin-2-yl)-N-(5-fluoropyridin-3-yl)-5-oxopyrrolidine-2-carboxamide (Compound 14)

Toluene was degassed by argon bubbling for at least 30 min at 20-30° C., added tris (dibenzylideneacetone)-dipalladium (0) 0.095 gm, 0.000103 moles) and R—(+)—BINAP (0.13 gm, 0.000209 moles) was stirred at 20-30° C. for 1 hrs, compound 8 (10.00 gm, 0.02079 moles), compound 11 (3.17 gm, 0.02287 moles) followed by potassium carbonate (3.45 gm, 0.02496 moles), the reaction mass was heated to reflux until the reaction completion, then the mixture is cooled to 50-60° C., toluene layer was successively washed with 50 ml water followed by addition of 0.80 gm N-acetyl-L-cysteine and the mixture was stirred 1 hrs at 50-60° C. followed by toluene layer was successively washed with 50 ml water twice, toluene layer was distilled off under reduced pressure to obtained crude compound 12, crude product was dissolved in 100 ml ethanol at 60-70° C., then cooled to 20-25° C., precipitated product was stirred 4 hrs at 20-25° C. and filtered off, this was recrystallized with ethanol to obtained white crystalline solid compound 14, 3.66 gm, yield: 30.0%, HPLC Purity: >99.50%).

Example-38: Preparation of (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 13)

Toluene (50 mL) and Methylacetate (10 mL) was degassed by argon bubbling for at least 30 min at 20-30° C., added tris (dibenzylideneacetone)-dipalladium (0) (0.095 gm, 0.000103 moles) and R—(+)—BINAP (0.13 gm, 0.000209 moles) was stirred at 20-30° C. for 1 hrs, compound 10 (10.00 gm, 0.02079 moles), compound 11 (3.17 gm, 0.02287 moles) followed by potassium carbonate (3.45 gm, 0.02496 moles), the reaction mass was heated to reflux until the reaction completion, then the mixture is cooled to 50-60° C., toluene layer was successively washed with 50 mL water followed by addition of 0.80 gm N-acetyl-L-cysteine and the mixture was stirred 1 hrs at 50-60° C. followed by toluene layer was successively washed with 50 mL water twice, toluene layer was distilled off under reduced pressure charged ethylacetate 25 mL and heated to 55-65° C. and charged 25 mL heptane then stirred 1 hr at 50-60° C., cooled slowly to 20-25° C. and stirred 4-5 hrs at 20-25° C., obtained solid was filtered off and washed with 1:2 mixture of ethylacetate:heptane mixture dried under vacuum at 45-55° C. to produce compound 13, 11.0 g, yield: 91.0%, HPLC Purity: >99.47%, Chiral purity: >99.70%). The obtained solid was Ivosidenib Form T5.

Example-39: Preparation of (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 13) Form T11

Compound 13 (10.0 gm, 0.0207 moles) dissolved in toluene (20 mL) and heated to 55-65° C., added slowly n-heptane (15 mL) at 55-65° C., over the period of 20-30 min then added Form T11 seeding at 55-65° C., stirred the obtained mass was 1 hrs at 55-65° C., slowly cool to 20-30° C. then added n-heptane (25 mL) then stirred for 3-4 hrs at 20-30° C., obtained solid was filtered off to produce compound 13 form T11, 5.7 gm, yield: 57.0%, HPLC Purity: >99.70%, diastereomeric isomer: <0.10%.

Example-40: Preparation of (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 13) Form T11

Compound 13 (1.0 gm, 0.00171 moles) dissolved in isoamyl alcohol (2 mL) and heated to 65-75° C., added slowly n-heptane (3 mL) at 65-75° C., stirred 1 hr at 65-75° C. then cooled to 40-50° C. then stirred 30 min at 20-25° C. then cooled to 20-25° C., charged 4 mL heptane and stirred 4 hrs at 20-25° C., obtained product was filtered off and washed with 1:2 mixture of isoamyl alcohol:heptane mixture 3 mL and dried to produce compound 13 form T11, 0.72 g, yield: 72.0%, HPLC Purity: >99.70%, diastereomeric isomer: <0.10%.

Example-41: Preparation of (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 13) Form T11

Toluene (10 mL) was degassed by argon bubbling for at least 30 min at 20-30° C., added tris (dibenzylideneacetone)-dipalladium (0) (0.009 g, 0.000009 moles) and R—(+)—BINAP (0.13 gm, 0.00002 moles) was stirred at 20-30° C. for 1 hrs, compound 10 (1.00 g, 0.002079 moles), compound 11 (0.32 g, 0.0023 moles) followed by potassium carbonate (0.57 g, 0.00412 moles), the reaction mass was heated to reflux until the reaction completion, then the mixture is cooled to 50-60° C., toluene layer was successively washed with 50 mL water twice distilled off under reduced pressure charged toluene 2 mL and heated to 55-65° C. and added 1 mL heptane then added Ivosidenib Form T11 seeding then stirred 1 hrs at 50-60° C., cooled slowly to 20-25° C. and stirred 4-5 hrs at 20-25° C., obtained solid was filtered off and washed with 1:1 mixture of Toluene:heptane mixture dried under vacuum at 45-55° C. to produce compound 13, 0.72 g, yield: 72.0%, HPLC Purity: >99.50%, Chiral purity: >99.80%).

Example 42: Chiral enrichment of compound 10 ML to obtain (S)—N—((S)-1-(2-chlorophenyl)-2-((3, 3-difluorocyclobutyl)amino)-2-oxoethyl)-N-(5-fluoropyridin-3-yl)-5-oxopyrrolidine-2-carboxamide in excess (Compound 9+10)

A compound 10 mother liquor was distilled off under vacuum at 40-45° C. to get residue (5 g, 0.0104 moles, Desired: ~35%, Undesired: ~65%) was stirred in Toluene (10 ml) and piperidine (1.16 gm, 0.0136 moles) and heated to 75-80° C. The resulting mixture was stirred at 75-80° C. for 4 hrs. Cool to 20-25° C., the obtained solid was filtered off and washed with toluene (5 mL). The product was dried under vacuum to afford solid. (Wt. 3.0 gm, HPLC purity >99.00%, Chiral Purity: >65.0%, 35.0%).

Example 43: Chiral separation of compound 8 to obtain (S)—N—((S)-1-(2-chlorophenyl)-2-((3, 3-difluorocyclobutyl)amino)-2-oxoethyl)-N-(5-fluoropyridin-3-yl)-5-oxopyrrolidine-2-carboxamide (Compound 10)

A racemic mixture of compound 8 (20 g, 0.0416 mole) obtained by Example no. 9 was added in methyl acetate (30 mL) and TFE 0.80 gm the resulting mass was heated to 65° C. MTBE (75 mL) was added, stirred the mass and cooled to 20-25° C. The solid thus obtained was filtered and washed with MTBE (40 mL). The mass was dried under vacuum to afford white solid. (Wt. 8.0 g, Chiral purity 99.93%, undesired isomer 0.07%).

Example 44: Chiral enrichment and separation of compound 10 ML to obtain (S)—N—((S)-1-(2-chlorophenyl)-2-((3, 3-difluorocyclobutyl)amino)-2-oxoethyl)-N-(5-fluoropyridin-3-yl)-5-oxopyrrolidine-2-carboxamide (Compound 10)

A compound 10 mother liquor was distilled off under vacuum at 40-45° C. to get residue (20 g, 0.04159 moles, Desired: ~35%, Undesired: ~65%) was stirred in Toluene (40 ml) and piperidine (4.43 gm, 0.0052 moles) and heated to 75-80° C. The resulting mixture was stirred at 75-80° C. for 6 hrs. Cool to 60-65° C., charged trifluoroethanol (0.6 g) and Methyl acetate (10 ml) the obtained solution was stirred for 30 min at 60-65° C., Cool to 20-25° C., obtained solid was stirred 4 hrs at 20-25° C. filtered off and washed with MTBE (50 mL). The product was dried under vacuum to afford solid. (Wt. 4.80 gm, HPLC purity >99.81%, Chiral Purity: >99.50%).

Example 45: Chiral enrichment and separation of compound 10 ML to obtain (S)—N—((S)-1-(2-chlorophenyl)-2-((3, 3-difluorocyclobutyl)amino)-2-oxoethyl)-N-(5-fluoropyridin-3-yl)-5-oxopyrrolidine-2-carboxamide (Compound 10)

A compound 10 mother liquor was distilled off under vacuum at 40-45° C. to get residue (18 g, 0.0374 moles, Desired: ~35%, Undesired: ~65%) was stirred in Toluene (60 ml) and piperidine 5 mL (1.16 gm, 0.0136 moles) and heated to 75-80° C. The resulting mixture was stirred at 75-80° C. for 4 hrs. Cool to 20-25° C., the obtained solid was filtered off and washed with toluene (5 mL). The product was dried under vacuum to afford solid. (Wt. 7.9 gm, HPLC purity >99.00%, Chiral Purity: >99.40%).

Example 46: Chiral enrichment and separation of compound 8 to obtain (S)—N—((S)-1-(2-chlorophenyl)-2-((3, 3-difluorocyclobutyl)amino)-2-oxoethyl)-N-(5-fluoropyridin-3-yl)-5-oxopyrrolidine-2-carboxamide (Compound 10)

A racemic mixture of compound 8 (330 g, 0.686 mole) was stirred in Toluene (1914 ml) and piperidine (70.12165 gm, 0.823507 moles) and heated to 70-80° C. The resulting mixture was stirred at 70-80° C. for 5 hrs. Cool to 50-60° C. and added second lot of piperidine (23.37 gm, 0.274 moles) and 66 ml of toluene. It was stirred for 30 min. Reaction mass was cooled to 25° C. and stirred for 4 hrs. It was filtered off and washed with 1% Piperidine in toluene solution (11.7 gm piperidine in 1320 ml toluene). Obtained solid was slurred in 0.5% HCl in water (660 ml×2) solution. Further solid was washed with 660 ml of water twice. The product was dried under vacuum to afford solid. (Wt. 176.5 gm, HPLC purity >99.00%, Chiral Purity: >99.50%).

Example 47: Direct preparation of Compound 10 from Compound 1: Preparation of (S)—N—((S)-1-(2-chlorophenyl)-2-((3, 3-difluorocyclobutyl) amino)-2-oxoethyl)-N-(5-fluoropyridin-3-yl)-5-oxopyrrolidine-2-carboxamide (Compound 10)

Compound 1 (100 gm, 0.6965 moles) was suspended in ethylformate 152 mL followed by addition of triethylamine (105.72 g, 1.0447 moles) the reaction mixture was refluxed for the 3-4 hrs, added 150 mL toluene and distilled off solvent under vacuum at 50-55° C. till residue volume reached up to 200-250 mL, cool reaction mass to 20-25° C., Charged MDC (700 mL) at 25-35° C. added triethyl amine (282 g, 2.7868 moles). The resulting solution was cooled to 0 to 5° C. and added POCl₃ (139.0 gm, 0.9065 mole). Reaction mass was stirred until completion (Monitored by GC) at 5-10° C. After completion of reaction it was quenched by aqueous ammonia solution (200 mL 30% aqueous ammonia solution and 1100 mL water. Organic layer was distilled off and charged 2, 2, 2 trifluoroethanol (600 mL) and it was cooled to 0-10° C. and added compound 6 ((1-(2-chlorophenyl)-N-(5-fluoropyridin-3-yl)methanimine) (131 g, 0.5582 mole)) and compound 7 (((S)-5-oxopyrrolidine-2-carboxylic acid) (81.0 g, 0.6273 mole)) at 0-10° C. and stirred for 1h (monitored by HPLC) at 0-10° C. and raised temperature to 20-25° C. then stirred for 4-5 hrs. After completion of reaction trifluoroethanol was distilled off under vacuum at 50-55° C. till residue volume reached up to 300-350 mL, and charged toluene and distilled off again. Charged 1000 mL Toluene at 40-45° C., organic layer was washed with 1% diluted HCl, 5% sodium carbonate solution at 40-50° C., then cooled to 20-25° C. and added piperidine in to it under stirring and reaction mass was heated to 70-80° C. Cooled and filter the precipitated product and washed it with 1% Piperidine in toluene solution. Obtained solid was slurred in 0.5% HCl in water (660 ml×2) solution. Further solid was washed with 660 ml of water twice. The product was dried under vacuum to afford solid. (Wt. 90-105 gm, HPLC purity >99.0%, Chiral Purity: >99.9%).

Examples for the Preparation of Solid Dispersion of Ivosidenib

Example 48: Preparation of Amorphous Solid Dispersion of Ivosidenib with Copovidone Ivosidenib (Form T11) 0.2 g and copovidone (0.2 g) were dissolved in methanol (10 mL) at 22-25° C. Reaction mixture was filtered through Hy-flo to remove any undissolved particlulate. The clear solution was subjected to rota-vapor distillation under reduced pressure at 40-45° C. Solid material was obtained and isolated at 22-25° C. The obtained solid was premix amorphous form of Ivosidenib with 50% copovidone (w/w ratio).

Example 49: Preparation of Amorphous Solid Dispersion of Ivosidenib with Copovidone Ivosidenib (Amorphous) 0.20 g and copovidone (0.20 g) were dissolved in methanol (10 mL) at 22-25° C. Reaction mixture was filtered through Hy-flo to remove any undissolved particulate. The clear solution was subjected to rota-vapor distillation under reduced pressure at 40-45° C. Solid material was obtained and isolated at 22-25° C. The obtained solid was premix amorphous form of Ivosidenib with 50% copovidone (w/w ratio).

Example 50: Preparation of Amorphous Solid Dispersion of Ivosidenib with HPMC

Ivosidenib (Form T11) 0.2 g and hydroxypropyl methylcellulose (HPMC) 0.2 g were dissolved in methanol (30 mL) at 40-45° C. Reaction mixture was cooled to 22-25° C. and filtered through Hy-flo to remove any undissolved particulate. The clear solution was subjected to rota-vapor distillation under reduced pressure at 40-45° C. Solid material was obtained and isolated at 22-25° C. The obtained solid was premix amorphous form of Ivosidenib with 50% HPMC (w/w ratio).

Example 51: Preparation of Amorphous Solid Dispersion of Ivosidenib with HPMC

Ivosidenib (Amorphous) 0.20 g and hydroxypropyl methylcellulose (HPMC) 0.20 g were dissolved in methanol (40 mL) at 40-45° C. Reaction mixture was cooled to 22-25° C. and filtered through Hy-flo to remove any undissolved particulate. The clear solution was subjected to rota-vapor distillation under reduced pressure at 40-45° C. Solid material was obtained and isolated at 22-25° C. The obtained solid was premix amorphous form of Ivosidenib with 50% HPMC (w/w ratio).

Example 52: Preparation of Ivosidenib Form T14

Ivosidenib (amorphous) 4.0 g was taken in a 50 mL reaction vessel and dissolved in 8.0 mL methanol at 25±1° C. with overhead stirring at 300 rpm and obtained a clear solution. The reaction mixture was maintained under stirring for 66-72 hours at 25±1° C. The reaction mixture was filtered under vacuum and suck dried for 10-20 minutes and further dried at 30° C. under vacuum. The obtained solid was isolated at 20-25° C. to obtain Ivosidenib hydrate designated as Form T14 (Yield: 3.4 g).

Example 53: Preparation of Ivosidenib Form T15

Ivosidenib (amorphous) 9.0 g was taken in a 50 mL reaction vessel with overhead stirring and added 4.0 mL methanol under stirring at 300 rpm and obtained a clear solution at 25° C. The clear solution was kept under stirring for 16-18 hours at 25° C. The reaction mixture was filtered and suck dried for 10-15 minutes to obtain Ivosidenib Form T15 (Yield: 7.2 g).

Example 54: Preparation of Ivosidenib Form T15

Ivosidenib (amorphous) 4.9 g was taken in a 50 mL reaction vessel with overhead stirring and added 10.0 mL methanol under stirring at 300 rpm and obtained a clear solution at 25° C. The clear solution was kept under stirring for 16-18 hours at 25° C. The reaction mixture was filtered and suck dried for 10-15 minutes to obtain Ivosidenib Form T15 (Yield: 3.2 g).

The invention claimed is:
1. Crystalline Form T11 of Ivosidenib, which is characterized by data selected from one or more of the following:
   i. an XRPD pattern having peaks at 14.3, 15.9, 21.2, 22.7 and 23.8 deg-2-theta±0.2 deg 2-theta;
   ii. an XRPD pattern as depicted in FIG. 12;
   iii. a solid state $^{13}$C—NMR spectrum with peaks at 178.4, 172.3, 151.8, 147.7 and 131.3 ppm±0.2 ppm;
   iv. a solid state $^{13}$C—NMR spectrum having the following chemical shift absolute differences from a peak at 57.8 ppm±2 ppm of 120.6, 114.5, 94.0, 89.9 and 73.5 ppm±0.1 ppm;
   v. a solid state $^{13}$C NMR spectrum having chemical shift difference from a peak at 178.4 ppm±1 ppm of 120.6 ppm±0.1 ppm;
   vi. a solid state $^{13}$C—NMR spectrum substantially as depicted in FIG. 27; or combinations of (i)-(vi).
2. A crystalline form of Ivosidenib according to claim 1, which is characterized by an XRPD pattern having peaks at

14.3, 15.9, 21.2, 22.7 and 23.8 deg-2-theta±0.2 deg 2-theta, and also having one, two, three, four or five additional peaks selected from 8.6, 17.4, 19.3, 26.2 and 29.0 deg-2-theta±0.2 deg 2-theta.

3. A process for preparing a pharmaceutical composition and/or formulation comprising combining the crystalline form of Ivosidenib according to claim 1 with at least one pharmaceutically acceptable excipient.

4. A process for preparing a solid dispersion, comprising combining the crystalline form of Ivosidenib according to claim 1 and at least one pharmaceutically acceptable solid-dispersion polymeric carrier.

5. The process according to claim 3, wherein the pharmaceutically acceptable solid-dispersion polymeric carrier is selected from: a polyvinyl pyrrolidone, a polyethylene glycol and a polymethacrylate, a cyclodextrin, a cellulosic polymer, a methacrylic acid-methyl methacrylate copolymer, an acrylic acid-methacrylate polymer, or a polyol or a polyol polymer.

* * * * *